United States Patent [19]
Nishi et al.

[11] Patent Number: 6,013,621
[45] Date of Patent: *Jan. 11, 2000

[54] METHOD OF TREATING PSYCHOSIS AND/OR HYPERACTIVITY

[75] Inventors: Akinori Nishi, Fukuoka, Japan; Gretchen L. Snyder, New York, N.Y.; Allen A. Fienberg, New York, N.Y.; Paul Greengard, New York, N.Y.

[73] Assignee: The Rockfeller University, New York, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 08/953,442

[22] Filed: Oct. 17, 1997

[51] Int. Cl.$^7$ .................................................. A61K 38/00
[52] U.S. Cl. .................................................. 514/2
[58] Field of Search .................................................. 514/2

[56] References Cited

U.S. PATENT DOCUMENTS 5,777,195  7/1998  Fienberg et al. .

FOREIGN PATENT DOCUMENTS

WO 95/34306  12/1995  WIPO .

OTHER PUBLICATIONS

Aitkin A. et al. (1982), Eur. J. Biochem., 126:235–246.
Aperia A. et al. (1991), Proc. Natl. Acad. Sci. USA, 88:2798–2801.
Beaurepaire et al. (1995) 121:323–7.
Begley, D.J. et al. (1990), J. of Neurochem., 55:1222–1230.
Boer et al. (1995) Psychopharmcology 121:317–22.
Borlongan et al. (1996) Surg. Neurol. 46:384–8.
Braff, D.L., and Geyer, M.A. (1990), Arch Gen Psychiatry, 47:181–188.
Cooper DM et al. (1995), Nature, 374:421–424.
Dawson, T.M. (1996) Annals of Neurology 40:559–60.
Dawson et al., (1993), Proc. Natl. Acad. Sci., 90:9808–9812.
Dolan et al. (1995) Nature 378:180–2.
Dragunow M. et al. (1990), Neuroscience, 37:287–94.
Fitzgerald LW et al.(1995), J. Neurosci., 15:2453–61.
Gerfen CR et al (1990), Science, 250: 1429–1432.
Ghasemzadeh MB et al.(1996), Molec Pharmacol. ,49:852–859.
Halpain S et al (1990), Nature, 343:369–372.
Hemmings Jr Hc et al(1984), Nature, 310: 503–505.
Hemmings Jr HC et al.(1986), J .Neurosci., 6: 1469–1481.
Karlsson P et al. (1995), Psychopharmacology, 121: 309–16.
King MM et al. (1984), J. Biol. Chem .,259:8080–8083.
Levine et al. (1994) Lancet 344:59–60.
Matsuura et al. (1996) Brain Res. 733:101–4.
Nestler, E.J. (1997) Nature 385:578–9.
Okubo et al. (1997) Nature 385:634.
Onali P et al. (1985), Mol. Pharmacol., 28: 138–145.
Ouimet CC et al. (1984), J. Neurosci .,4: 111–124.
Polli JW and Kincaid RL (1994), J. Neurosci., 14: 1251–1261.
Seeman P and Van Tol HH (1994), Trends in Pharmacol. Sci., 15:264–70.
Sibley et al. (1992), Trends in Pharmacol., Sci., 13: 61–69.
Sipes T. A. and Geyer M.A. (1995), Psychopharmacology, 117:41–48.
Snyder GL et al. (1996), Soc. Neurosci. Abst., 22: 380 (Abst. 153.11).
Snyder et al. (1995) Nature Med. 1:32–6.
Snyder GL et al.(1992), J. Neurosci ., 12: 3071–3083.
Steiner et al. (1997) Nature Med. 3:421–8.
Stoof JC and Kebabian JW (1981), Nature, 294: 366–8.
Surmeier DJ et al.(1994) , Neuron , 14:385–397.
Surmeier DJ et al. (1992), Proc. Natl. Acad. Sci., USA, 89: 10178–10182.
Surmeier DJ et al. (1996), J. Neurosci., 16: 6579–91.
Thastrup O et al.(1990), Proc. Natl. Acad. Sci., USA 87: 2466–70.
Walaas SI et al. (1983), Nature, 301: 69–71.
Walaas SI and Greengard P (1984), J. Neurosci, 4 :84–98.
Wera et al. (1994) Med. Hypotheses 43:132–4.
Nishi et al., 1997, J. Neuroscience, 17:8147–55.
Reynolds, 1996, Royal Pharmaceutical Society, 672–73.
Varty et al., 1995, Psychopharmacology, 122:15–26.
Wan et al., 1993, Psychopharmacology, 113:103–9.
Albert et al., 1998, Society for Neuroscience Abstract, 24:754.
Guitart et al., 1992, J Neurochem, 59:1164–7.
Gong et al., 1996, Brain Research, 741:95–102.
Grebb, 1990, Nakazawa ed.: Raniguchi Symosia on Brain Science, NO 14. Bop;pgica; Basis of Schizophrenic Disorders, 14th International Symposium Datata, 80–2.
Wan et al., 1996, Neuropsychoharmacology, 14:165–74.
Mermelstein et al., 1996, Society for Neuroscience Abstract, 22:2028.
Tanaka et al. Int. Congr. Ser., 1116, 57–65 (Abstract), 1996.

*Primary Examiner*—Raymond Henley, III
*Attorney, Agent, or Firm*—Klauber & Jackson

[57] ABSTRACT

The present invention discloses the bidirectional regulation of DARPP-32 phosphorylation by dopamine and dopamine D1 and D2 receptors. This disclosure leads to new methodology in the treatment of schizophrenia and related disorders. In addition, the present invention provides methods for identifying agents that can be used in such treatment.

5 Claims, 10 Drawing Sheets

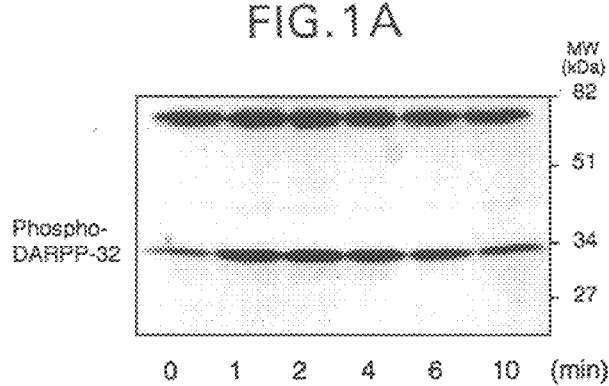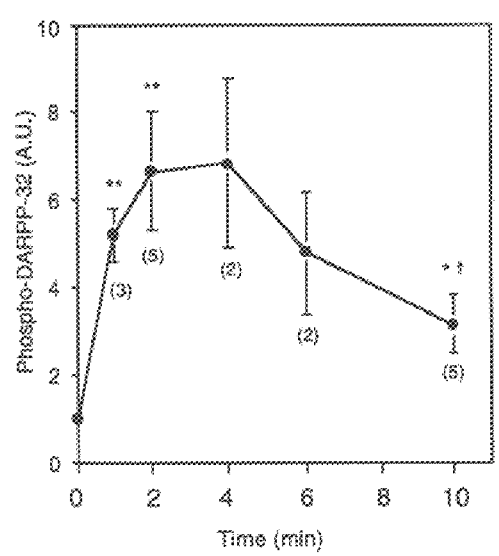

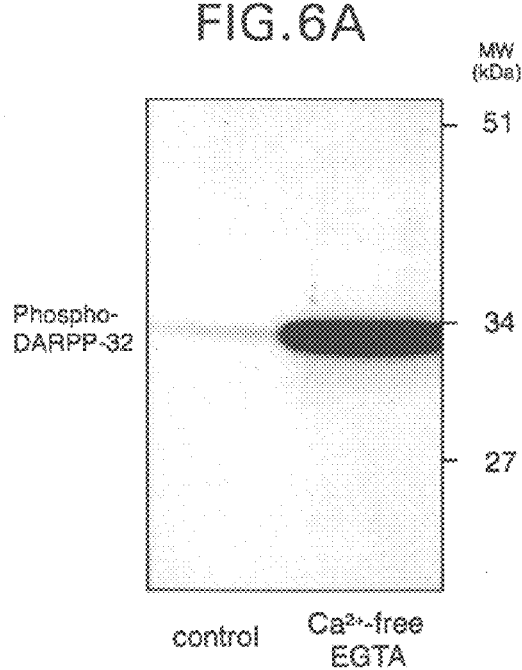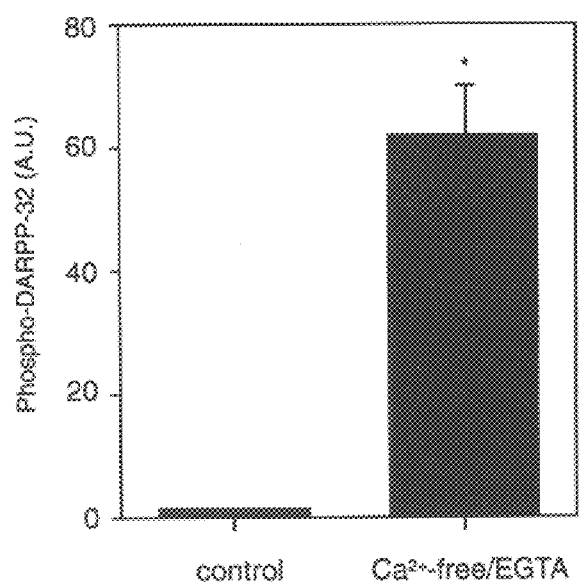

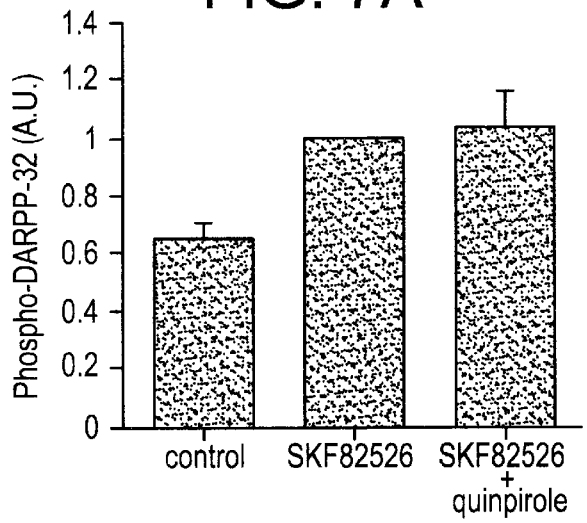
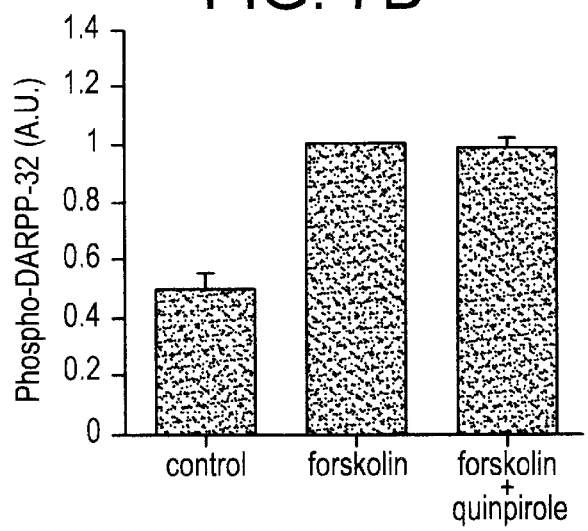
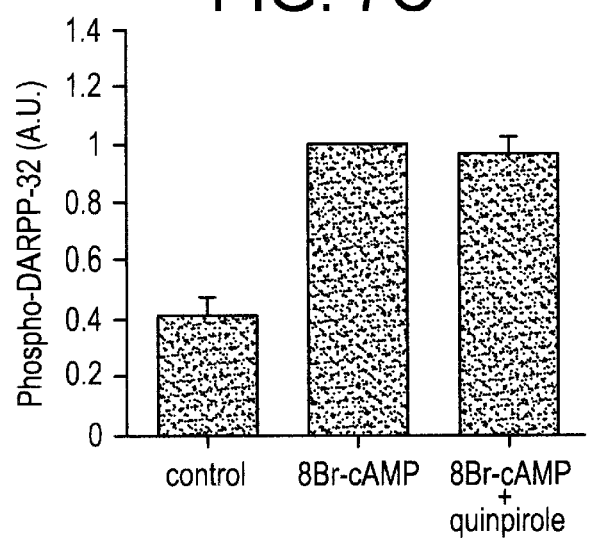

METHOD OF TREATING PSYCHOSIS AND/OR HYPERACTIVITY

GOVERNMENTAL SUPPORT

The research leading to the present invention was supported, at least in part, by a grant from the U.S. Public Health Service, Grant No. MH40899. Accordingly, the Government may have certain rights in the invention.

FIELD OF THE INVENTION

The present invention provides a method for treating schizophrenia and related disorders. In addition, the present invention provides methods for identifying agents that can be used in the treatment of schizophrenia and related disorders.

BACKGROUND OF THE INVENTION

DARPP-32, a dopamine- and cyclic AMP (cAMP)-regulated phosphoprotein having a molecular weight of 32 kilodaltons, is a cytosolic protein which is selectively enriched in medium-sized spiny neurons in neostriatum (Ouimet et al., 1984; Walaas and Greengard, 1984). DARPP-32 is phosphorylated by cAMP-dependent protein kinase (PKA) on a single threonine residue, thr$^{34}$, resulting in its conversion into a potent inhibitor of protein phosphatase-1 (Hemmings et al., 1984). DARPP-32 can be dephosphorylated and inactivated in vitro by the calcium/calmodulin-dependent protein phosphatase, calcineurin (King et al., 1984). Dopamine has been shown to stimulate the phosphorylation of DARPP-32 in neostriatum by activation of a biochemical cascade involving stimulation of D1 receptors, activation of adenylyl cyclase, increased cAMP formation and increased activity of PKA (Walaas and Greengard, 1984). The selective enrichment of DARPP-32 in dopaminoceptive neurons and its regulation by dopamine strongly indicate that DARPP-32, by regulating protein phosphatase-1 activity, plays a key role in mediating the effects of dopamine on these cells. The control of protein phosphatase-1 activity by DARPP-32 is likely to have a significant role in the regulation of neuronal excitability. For instance, in neostriatum, dopamine-mediated effects on the function of calcium channels (Surmeier et al., 1994), voltage-dependent sodium channels (Surmeier et al., 1992; Schiffman et al., 1994) and Na$^+$,K$^+$-ATPase (Aperia et al., 1991) are regulated directly or indirectly by protein phosphatase-1.

Medium-sized spiny neurons of the neostriatum and nucleus accumbens receive dopaminergic input from cell bodies in the midbrain (Anden et al., 1964; Poirier and Sourkes, 1965; Swanson, 1982). To date, five dopamine receptor subtypes have been identified which constitute two major subclasses, a D1 subfamily (D1 and D5 subtypes) and a D2 subfamily (D2, D3 and D4 subtypes) (Sibley and Monsma, 1992). D1 and D2 dopamine receptors are abundantly expressed on cell bodies and dendritic processes of medium spiny neurons (Levey et al., 1993). Messenger RNAs coding for each of the other dopamine receptor subtypes (i.e., D3, D4, and D5) have been isolated from individual neostriatal neurons (Surmeier et al., 1996), but whether these receptor proteins are expressed in medium spiny neurons and how they functionally interact with D1 and D2 receptors is still unclear.

There is considerable evidence for either synergistic or opposing interactions of D1-like and D2-like dopamine receptors at the biochemical, physiological, and behavioral level (see Jackson and Westlind-Danielsson, 1994 for review). Biochemically, D1 and D2 receptors have opposing actions on the activity of adenylyl cyclase in neostriatal neurons; whereas activation of D1 receptors increases cAMP formation by adenylyl cyclase, D2 receptors inhibit adenylyl cyclase activity (Stoof and Kebabian, 1981). Recent studies have shown that D2-like dopamine receptors via interactions with specific G-proteins, can be coupled to multiple effector systems, including calcium channels, potassium channels and phospholipase C (for review, see Huff, 1996). For example, Yan et al., (1996) have shown that D2 receptors on neostriatal neurons negatively couple to calcium channels through a $G_{I/o}$ class protein. In addition, activation of D2 receptors apparently decreases sodium currents in medium spiny neostriatal neurons through a membrane-delimited pathway and increases these currents through a soluble second messenger pathway (presumably involving inhibition of adenylyl cyclase) (Surmeier et al., 1992).

Schizophrenia is a clinical ailment which has an immense effect on the public health. For example, it has been estimated that as many as 50% of the homeless people living in the United States are schizophrenic. [Bachrach, In: Treating the Homeless Mentally Ill, Washington, D.C., American Psychiatric Press, 1340, Lamb et al. ed. (1992)]. In addition, approximately 2.5% of the total dollars spent for health care in the United States is spent in the treatment of schizophrenia [Rupp et al., *Psychiatric Clin. North Am.* 16:413–423 (1993)]. Unfortunately, at present, there exists no reliable or effective means of treating schizophrenia.

Therefore, there is a need to provide new drugs assays which can be used to develop new drugs to treat schizophrenia. Further there is a need to provide new drugs which can be used in such treatment.

The citation of any reference herein should not be construed as an admission that such reference is available as "Prior Art" to the instant application.

SUMMARY OF THE INVENTION

The present invention provides a novel means of exploiting the determination that the phosphorylation of DARPP-32 is under bidirectional regulation involving dopamine, dopamine D1 and D2 receptors, and calcineurin. The present invention further provides new methodology in the treatment of diseases such as schizophrenia, Parkinson's disease, Tourette's syndrome, drug abuse and attention deficit disorder. In addition, the present invention provides methods for identifying agents that can be used in such treatment.

Therefore, the present invention provides a method of treating a schizophrenic patient that comprises administering an agent to the patient that inhibits the dephosphorylation of thr$^{34}$-phosphorylated DARPP-32. In a preferred embodiment of this type the agent inhibits calcineurin. In a more preferred embodiment the agent inhibits calcineurin by binding to calcineurin.

Preferably the agent readily passes through the blood brain barrier. One such agent is FK506. Alternatively, the agent can be modified or otherwise altered so that it can cross or be carried across the blood brain barrier.

The present invention also provides a method of identifying an agent for use in the treatment of a schizophrenic patient. The agent is selected for its ability to inhibit the dephosphorylation of thr$^{34}$-phosphorylated DARPP-32 by calcineurin. One such embodiment comprises using calcineurin or a fragment or analog thereof in a drug screen. Preferably calcineurin is bound to a solid support. Compounds that bind to calcineurin or the fragment or analog thereof are selected as potential agents.

Alternatively, a potential agent is contacted with calcineurin and a phosphorylated substrate for calcineurin. The amount of dephosphorylation of the substrate is determined and a potential agent is identified if a decrease in the dephosphorylation of substrate is determined in the presence of the potential agent. In preferred embodiments of this type, the phosphorylated substrate is thr$^{34}$-phosphorylated DARPP-32.

In another embodiment a potential agent is administered to an animal along with a dopamine D2 receptor agonist. In this case the administration of the D2 agonist alone results in a diminished percentage of prepulse inhibition. The response of the mouse to prepulse inhibition is measured and an agent is selected when the response to prepulse inhibition is statistically significantly increased in the presence of the potential agent relative to that determined in the absence of the potential agent. In a preferred embodiment of this type the selected agent is also administered to a DARPP-32 knockout mouse. A DARPP-32 knockout mouse has been shown to have a diminished percent prepulse inhibition relative to the wildtype mouse, see below. The response of the knockout mouse to prepulse inhibition is then determined. An agent is identified when the response to prepulse inhibition is not statistically significantly increased in the DARPP-32 knockout mouse in the presence of the selected agent relative to that determined in the absence of the selected agent.

In a preferred embodiments of this type the animal is a mammal. In one such embodiment the animal is a rodent. In a more preferred embodiment of this type the rodent is a mouse.

As would be clearly understood by a person of ordinary skill in the art, any and/or all of the above embodiments for identifying an agent for use in the treatment of a schizophrenic patient can be combined to form additional drug screens and assays, all of which are contemplated by the present invention.

Accordingly, it is a principal object of the present invention to provide a method of ameliorating one or more symptoms of schizophrenia by administering an agent that enhances the phosphorylation state of threonine-34 of DARPP-32.

It is a further object of the present invention to provide an agent that can ameliorate a symptom of schizophrenia by blocking the effect of calcineurin on phosphorylated DARPP-32.

It is a further object of the present invention to provide an agent that blocks the effect of calcineurin on phosphorylated DARPP-32 by binding directly to calcineurin.

It is a further object of the present invention to provide a method of selecting an agent that can ameliorate a symptom of schizophrenia by blocking the effect of calcineurin on phosphorylated DARPP-32.

It is a further object of the present invention to provide a method of screening potential drugs in order to select an agent that can potentially ameliorate a symptom of schizophrenia by blocking the effect of calcineurin on phosphorylated DARPP-32.

These and other aspects of the present invention will be better appreciated by reference to the following drawings and Detailed Description.

BRIEF DESCRIPTION OF THE DRAWINGS

FIG. 1 depicts the effect of dopamine on the level of phosphorylated DARPP-32 in neostriatum. Slices were incubated with dopamine (100 $\mu$M) in the presence of the dopamine uptake inhibitor nomifensine (10 $\mu$M) for the indicated times. In FIG. 1A the phosphorylated DARPP-32 was detected at a molecular mass of approximately 32 kDa using a monoclonal antibody (Ab), mAb-23, against thr$^{34}$-phosphorylated DARPP-32. Note that the phospho-DARPP-32 antibody also detected a cross-reactive protein band at a molecular mass of approximately 75 kDa, the levels of which were not affected by dopamine In FIG. 1B the total DARPP-32 was detected in the same membrane as shown in FIG. 1A using a monoclonal Ab (C24-5a) against DARPP-32. In FIG. 1C the amount of phospho-DARPP-32 was quantitated by densitometry, and the data were normalized to values obtained with untreated tissue. Data represent mean ±SEM for the number of experiments shown in parentheses. * P <0.05, ** P <0.01 compared with 0 min; †P<0.05 compared with 2 min.

FIG. 4 depicts the effect of the antipsychotic drug raclopride on the level of phosphorylated DARPP-32 in neostriatum (FIG. 4A) and nucleus accumbens (FIG. 4B). Slices were incubated for a total of 20 minutes. Raclopride (1 $\mu$M) was added at 0 min, quinpirole (100 nM) at 10 min and SKF82526 (1 $\mu$M) at 15 min of incubation. The amount of phospho-DARPP-32 was quantitated by densitometry, and the data were normalized to values obtained with SKF82526 alone.

FIG. 6 depicts the effect of Ca$^{2+}$-free/EGTA medium on the level of phosphorylated DARPP-32 in neostriatum.

Slices were incubated in control or $Ca^{2+}$-free/EGTA medium for 20 minutes. In FIG. 6A phosphorylated DARPP-32 was detected using a phosphorylation-state specific antibody (Ab), mAb-23. In FIG. 6B the amount of phospho-DARPP-32 was quantitated by densitometry, and the data were normalized to values obtained with control. Data represent means ±SEM for 4 experiments. * $P<0.01$ compared with control.

FIG. 7 depicts the absence of effect of a D2 agonist, quinpirole, on the level of phosphorylated DARPP-32 in $Ca^{2+}$-free/EGTA medium. Neostriatal slices were incubated in $Ca^{2+}$-free/EGTA medium for a total of 20 minutes. Buffer was replaced by $Ca^{2+}$-free/EGTA medium at 0 minutes, quinpirole (1 $\mu M$) was added at 10 min and SKF82526 (1 mM), in FIG. 7A, forskolin (10 $\mu M$) in FIG. 7B, or 8-bromo-cAMP (1 mM) in FIG. 7C, at 15 minutes of incubation. The amount of phospho-DARPP-32 was quantitated by densitometry, and the data were normalized to values obtained with SKF82526, forskolin or 8-bromo-cAMP alone. Data represent means ±SEM for 3 to 4 experiments.

DETAILED DESCRIPTION OF THE INVENTION

Figure 2A:
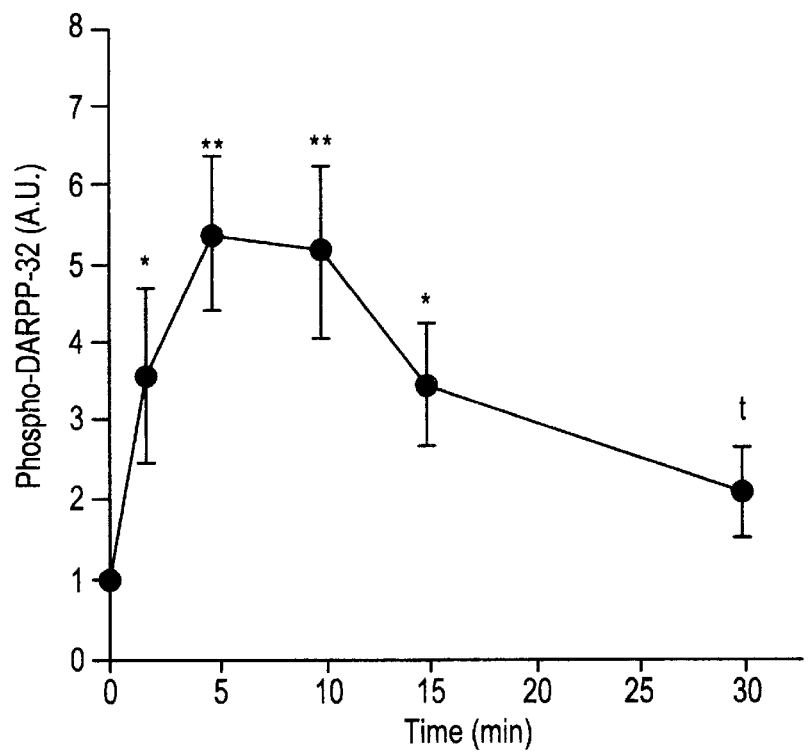
In FIG. 2A slices were incubated with 1 $\mu$M SKF82526, whereas in FIG. 2B slices were incubated with 1 $\mu$M quinpirole for the indicated times. The amount of phospho-DARPP-32 was quantitated by densitometry, and the data were normalized to values obtained with untreated tissue. Data represent means ±SEM for 4 to 12 experiments. * P<0.05, ** P<0.01 compared with 0 min; †P<0.05 compared with 5 min.

Although the present invention does not rely on any one particular metabolic model or scheme, it can be best understood in the context of the unexpected demonstration disclosed herein that DARPP-32 phosphorylation is regulated in mouse neostriatum through the opposing actions of D1-like and D2-like dopamine receptors. Previous reports [Walaas et al., (1983); Walaas and Greengard, (1984)] had shown that dopamine stimulates D1-like dopamine receptors in rat striatum, leading to sequential activation of adenylyl cyclase and cAMP-dependent protein kinase; and phosphorylation of DARPP-32 on threonine-34 ($thr^{34}$). Therefore the results provided herein indicate that dopamine-stimulated DARPP-32 phosphorylation is a D1 receptor-mediated effect, and furthermore demonstrate that the activation of D2-like dopamine receptors strongly reduces both the basal level of DARPP-32 phosphorylation and the phosphorylation of DARPP-32 stimulated by SKF82526, forskolin and 8-bromo-cAMP. Thus, D1-like and D2-like dopamine receptors have opposing effects on the activity of DARPP-32. Furthermore, as demonstrated herein the effect of D2 receptors on DARPP-32 phosphorylation is calcium-dependent and mediated by an increase in intracellular $Ca^{2+}$ and an activation of calcineurin.

The present invention is consistent with the widely believed premise that a relative hyperactivity within mesolimbic and/or nigrostriatal dopaminergic systems contribute to the etiology of schizophrenia (Davis et al., 1991). This premise is based largely on studies of the mechanism of action of neuroleptic medications. Thus the therapeutic efficacy of antipsychotic drugs is linked to their ability to block dopamine receptors, particularly those which interact with D2-like dopamine receptors (Seeman, 1992). Indeed, typical antipsychotic drugs have been reported to antagonize the inhibitory effect of D2 receptors on adenylyl cyclase (Onali et al., 1985), to increase Fos expression (Dragunow et al., 1990) and to affect the expression of glutamate receptor subunits (Fitzgerald et al., 1995). Results disclosed herein demonstrate that raclopride, a widely-used antipsychotic, increases the phosphorylation of DARPP-32 in basal and D2 receptor-activated conditions in slices of neostriatum and nucleus accumbens, implicating a DARPP-32/protein phosphatase-1 pathway in the actions of this and other antipsychotic drugs. Raclopride also blocked D2-mediated inhibition of D1-stimulated DARPP-32 phosphorylation in neostriatum and nucleus accumbens. The nucleus accumbens is a target for mesolimbic dopaminergic projections (Swanson, 1982) that has been implicated in the genesis of psychotic symptoms (Davis et al., 1991).

The notion that the action of antipsychotic drugs might be mediated through increasing DARPP-32 phosphorylation is made more interesting by a recent report showing that treatment with a D1 antagonist (SCH39166) does not improve but actually worsens the symptoms of schizophrenia (Karlsson et al., 1995). D1 antagonists, like D2 agonists, would be expected to inhibit increases in DARPP-32 phosphorylation. The increased DARPP-32 phosphorylation, observed in response to raclopride treatment, would be expected to inhibit protein phosphatase-1 activity, resulting in an increase in the state of phosphorylation of various substrates which contribute to the regulation of neuronal excitability. Therefore it appears that the D1/DARPP-32/protein phosphatase-1 cascade regulates the state of phosphorylation and/or the activity of, the electrogenic sodium pump, $Na^+,K^+$-ATPase (Nishi et al., 1996), calcium channels (Surrneier et al., 1994), voltage-dependent sodium channels [Surmeier et al., (1992); Schiffman et al., (1994)] and the glutamate receptor subunit, NR1 (Snyder et al., 1996).

Therefore, present invention provides novel methodology for the treatment of diseases such as schizophrenia, Parkinson's disease, Tourette's syndrome, drug abuse and attention deficit disorder through the use of drugs that interfere with the calcineurin-dependent dephosphorylation of DARPP-32. Furthermore, the present invention provides methods for selecting and/or screening for drugs that can be used in treatment of these diseases.

Drug Screening

Initially a potential inhibitor of calcineurin could be obtained by screening a random peptide library produced by recombinant bacteriophage for example, [Scott and Smith, *Science*, 249:386–390 (1990); Cwirla et al., *Proc. Natl. Acad. Sci.*, 87:6378–6382 (1990); Devlin et al., *Science*, 249:404–406 (1990)] or a chemical library. Using the "phage method" very large libraries can be constructed ($10^6$–$10^8$ chemical entities). A second approach uses primarily chemical methods, of which the Geysen method [Geysen et al., *Molecular Immunology* 23:709–715 (1986); Geysen et al. *J. Immunologic Method* 102:259–274 (1987)] and the method of Fodor et al. [*Science* 251:767–773 (1991)] are examples. Furka et al. [*14th International Congress of Biochemistry*, Volume 5, Abstract FR:013 (1988); Furka, *Int. J. Peptide Protein Res.* 37:487–493 (1991)], Houghton [U.S. Pat. No. 4,631,211, issued December 1986] and Rutter et al. [U.S. Pat. No. 5,010,175, issued Apr. 23, 1991] describe methods to produce a mixture of peptides that can be tested as inhibitors of calcineurin dephosphorylation activity.

In another aspect, synthetic libraries [Needels et al., *Proc. Natl. Acad. Sci. USA* 90:10700–4 (1993); Ohlmeyer et al., *Proc. Natl. Acad. Sci. USA* 90:10922–10926 (1993); Lam et al., International Patent Publication No. WO 92/00252; Kocis et al., International Patent Publication No. WO 9428028, each of which is incorporated herein by reference in its entirety], and the like can be used to screen for inhibitors of calcineurin according to the present invention. Once a potential inhibitor is identified, chemical analogues can be either selected from a library of chemicals as are commercially available from most large chemical companies including Merck, GlaxoWelcome, Bristol Meyers Squib, Monsanto/Searle, Eli Lilly, Novartis and Pharmacia UpJohn, or alternatively synthesized de novo. The prospective agent (drug) can be placed into any standard assay to test its effect on the dephosphorylation of DARPP-32 by calcineurin. A drug is selected that inhibits the dephosphorylation.

The present invention contemplates screens for small molecules, analogs thereof, as well as screens for natural inhibitors that bind to and inhibit calcineurin in vivo. For example, natural products libraries can be screened using assays of the invention for molecules that antagonize calcineurin activity.

Blood Brain Barrier: In a preferred aspect, the agent can cross the blood-brain barrier, which would allow for intravenous or oral administration. Many strategies are available for crossing the blood-brain barrier, including but not limited to, increasing the hydrophobic nature of a molecule; introducing the molecule as a conjugate to a carrier, such as transferrin, targeted to a receptor in the blood-brain barrier; and the like. In another embodiment, the molecule can be administered intracranially or, more preferably, intraventricularly. In another embodiment, osmotic disruption of the blood-brain barrier can be used to effect delivery of agent to the brain ([Neuwelt] et al., 1995, Proc. Natl. Acad. Sci. USA ["Delivery of herpesvirus and adenovirus to nude rat intracerebral tumors after osmotic blood-brain barrier disruption", Oct. 10, 1995]). In yet another embodiment, an agent can be administered in a liposome targeted to the blood-brain barrier. Administration of pharmaceutical agents in liposomes is known (see Langer, 1990, Science 249:1527–1533; Treat et al., in *Liposomes in the Therapy of Infectious Disease and Cancer,* Lopez-Berestein and Fidler (eds.), Liss, New York, pp. 353–365 (1989); Lopez-Berestein, ibid., pp. 317–327; see generally ibid.) All of such methods are envisioned in the present invention.

Although some predictions have been made concerning the ability of molecules to pass through the blood-brain barrier, these predictions are at best speculative. The rate and extent of entry of a compound into the brain are generally considered to be determined primarily by partition coefficient, ionization constant(s), and molecular size. No single partition solvent system has emerged as a universally applicable model for brain penetration, although the octanol water system has received particular attention, and Hansch and coworkers have suggested that a partition coefficient in this system of about 100 is optimal for entry into the central nervous system (CNS) (Glave and Hansch, 1972, J. Pharm. Sci. 61:589; Hansch et al., 1987, J. Pharm. Sci., 76:663). In practice, the octanol-water partition system only provides a qualitative indication of the capability of a compound to cross the blood-brain barrier. For example, comparisons between known histamine $H_2$ receptor antagonists suggest that there is no such simple relationship between their brain penetration and octanol water partition coefficients (Young et al., 1988, *J. Med. Chem.* 31:656). Other factors, besides the octanol-water partition influence the propensity to cross the blood-brain barrier. Comparison of the ability of histamine H, receptor antagonists to cross the blood-brain barrier suggests that brain penetration may increase with decreasing over-all hydrogen binding ability of a compound (Young et al., supra). Begley et al. [J. Neurochem. 55:1221–1230 (1990)] herein incorporated by reference in its entirety, have more recently examined the ability of cyclosporin A to cross the blood-brain barrier. Methodology as used by Begley et al. includes: (1) measuring the brain uptake index (BUI) with the equation for a tritiated agent compound:

BUI=[(brain $^3$H/brain $^{14}$C) / (injectate $^3$H/ injectate $^{14}$C)]×100 where the $^{14}$C reference compound is $^{14}$C butanol or an analogous solvent; (2) Brain perfusion studies; (3) Intravenous bolus injection studies; and (4) Studies with cultured cerebral capillary endothelium.

Labels: Any of the potential agents and targets for the potential agents (e.g., calcineurin) or DARPP-32 (such as $^{32}$Pthr$^{34}$ phosphorylated DARPP-32) can be labeled. Suitable labels include enzymes, fluorophores (e.g., fluoroscene isothiocyanate (FITC), phycoerythrin (PE), Texas red (TR), rhodamine, free or chelated lanthanide series salts, especially $Eu^{3+}$, to name a few fluorophores), chromophores, radioisotopes, chelating agents, dyes, colloidal gold, latex particles, ligands (e.g., biotin), and chemiluminescent agents. When a control marker is employed, the same or different labels may be used for the receptor and control marker.

In the instance where a radioactive label, such as the isotopes $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re are used, known currently available counting procedures may be utilized. In the instance where the label is an enzyme, detection may be accomplished by any of the presently utilized colorimetric, spectrophotometric, fluorospectrophotometric, amperometric or gasometric techniques known in the art.

Direct labels are one example of labels which can be used according to the present invention. A direct label has been defined as an entity, which in its natural state, is readily visible, either to the naked eye, or with the aid of an optical filter and/or applied stimulation, e.g. U.V. light to promote fluorescence. Among examples of colored labels, which can be used according to the present invention, include metallic sol particles, for example, gold sol particles such as those described by Leuvering (U.S. Pat. No. 4,313,734); dye sole particles such as described by Gribnau et al. (U.S. Pat. No. 4,373,932) and May et al. (WO 88/08534); dyed latex such as described by May, supra, Snyder (EP-A 0 280 559 and 0 281 327); or dyes encapsulated in liposomes as described by Campbell et al. (U.S. Pat. No. 4,703,017). Other direct labels include a radionucleotide, a fluorescent moiety or a luminescent moiety. In addition to these direct labelling devices, indirect labels comprising enzymes can also be used according to the present invention. Various types of enzyme linked immunoassays are well known in the art, for example, alkaline phosphatase and horseradish peroxidase, lysozyme, glucose-6-phosphate dehydrogenase, lactate dehydrogenase, urease, these and others have been discussed in detail by Eva Engvall in Enzyme Immunoassay ELISA and EMIT in *Methods in Enzymology*, 70 419–439, 1980 and in U.S. Pat. No. 4,857,453.

Suitable enzymes include, but are not limited to, alkaline phosphatase and horseradish peroxidase. Other labels for use in the invention include magnetic beads or magnetic resonance imaging labels.

As exemplified herein, proteins can be labeled by metabolic labeling. Metabolic labeling occurs during in vitro incubation of the cells that express the protein in the presence of culture medium supplemented with a metabolic label, such as [$^{35}$S]-methionine or [$^{32}$P]-orthophosphate. In addition to metabolic (or biosynthetic) labeling with [$^{35}$S]-methionine, the invention further contemplates labeling with [$^{14}$C]-amino acids and [$^{3}$H]-amino acids (with the tritium substituted at non-labile positions).

Administration

According to the invention, the component or components of a therapeutic composition of the invention may be introduced parenterally, topically, or transmucosally, e.g., orally, nasally, or rectally, or transdermally. Preferably, administration is parenteral, e.g., via intravenous injection, and also including, but is not limited to, intra-arteriole, intramuscular, intradermal, subcutaneous, intraperitoneal, intraventricular, and intracranial administration.

In another embodiment, the therapeutic compound can be delivered in a vesicle, in particular a liposome [see Langer, Science 249:1527–1533 (1990); Treat et al., in *Liposomes in the Therapy of Infectious Disease and Cancer*, Lopez-Berestein and Fidler (eds.), Liss: New York, pp. 353–365 (1989); Lopez-Berestein, ibid., pp. 317–327; see generally ibid.]. To reduce its systemic side effects, this may be a preferred method for introducing the agent.

In yet another embodiment, the therapeutic compound can be delivered in a controlled release system. For example, the agent may be administered using intravenous infusion, an implantable osmotic pump, a transdermal patch, liposomes, or other modes of administration. In one embodiment, a pump may be used [see Langer, supra; Sefton, CRC *Crit. Ref Biomed. Eng.* 14:201 (1987); Buchwald et al., *Surgery* 88:507 (1980); Saudek et al., *N. Engl. J. Med.* 321:574 (1989)]. In another embodiment, polymeric materials can be used [see *Medical Applications of Controlled Release*, Langer and Wise (eds.), CRC Press: Boca Raton, Florida (1974); *Controlled Drug Bioavailability, Drug Product Design and Performance*, Smolen and Ball (eds.), Wiley: New York (1984); Ranger and Peppas, *J. Macromol. Sci. Rev. Macromol. Chem.* 23:61 (1983); see also Levy et al., *Science* 228:190 (1985); During et al., *Ann. Neurol.* 25:351 (1989); Howard et al., *J. Neurosurg.* 71:105 (1989)]. In yet another embodiment, a controlled release system can be placed in proximity of the therapeutic target, i.e., the brain, thus requiring only a fraction of the systemic dose [see, e.g., Goodson, in *Medical Applications of Controlled Release*, supra, vol. 2, pp. 115–138 (1984)].

Other controlled release systems are discussed in the review by Langer [*Science* 249:1527–1533 (1990)].

Pharmaceutical Compositions: In yet another aspect of the present invention, provided are pharmaceutical compositions of the above. Such pharmaceutical compositions may be for administration for injection, or for oral, topological, nasal or other forms of administration. In general, comprehended by the invention are pharmaceutical compositions comprising effective amounts of the agents of the invention together with pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc. or into liposomes. Hyaluronic acid may also be used. Such compositions may influence the physical state, stability, rate of in vivo release, and rate of in vivo clearance of the present proteins and derivatives. See, e.g., Remington's Pharmaceutical Sciences, 18th Ed. (1990, Mack Publishing Co., Easton, Pa. 18042) pages 1435–1712 which are herein incorporated by reference. The compositions may be prepared in liquid form, or may be in dried powder, such as lyophilized form.

Oral Delivery: Contemplated for use herein are oral solid dosage forms, which are described generally in Remington's Pharmaceutical Sciences, 18th Ed. 1990 (Mack Publishing Co. Easton, Pa. 18042) at Chapter 89, which is herein incorporated by reference. Solid dosage forms include tablets, capsules, pills, troches or lozenges, cachets or pellets. Also, liposomal or proteinoid encapsulation may be used to formulate the present compositions (as, for example, proteinoid microspheres reported in U.S. Pat. No. 4,925,673). Liposomal encapsulation may be used and the liposomes may be derivatized with various polymers (e.g., U.S. Pat. No. 5,013,556). A description of possible solid dosage forms for the therapeutic is given by Marshall, K. In: *Modern Pharmaceutics* Edited by G. S. Banker and C. T. Rhodes Chapter 10, 1979, herein incorporated by reference. In general, the formulation will include the agent and inert ingredients which allow for protection against the stomach environment, and release of the biologically active material in the intestine.

To ensure full gastric resistance a coating impermeable to at least pH 5.0 is useful. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e. powder; for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the protein (or derivative) may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, a-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential non-ionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the protein or derivative either alone or as a mixture in different ratios.

Additives which potentially enhance uptake of the agent are for instance the fatty acids oleic acid, linoleic acid and linolenic acid.

Controlled release oral formulation may be desirable. The agent could be incorporated into an inert matrix which permits release by either diffusion or leaching mechanisms, e.g., gums. Slowly degenerating matrices may also be incorporated into the formulation. Some enteric coatings also have a delayed release effect.

Another form of a controlled release of this therapeutic is by a method based on the Oros therapeutic system (Alza Corp.), i.e. the drug is enclosed in a semipermeable membrane which allows water to enter and push drug out through a single small opening due to osmotic effects.

Other coatings may be used for the formulation. These include a variety of sugars which could be applied in a coating pan. The therapeutic agent could also be given in a film coated tablet and the materials used in this instance are divided into 2 groups. The first are the nonenteric materials and include methyl cellulose, ethyl cellulose, hydroxyethyl cellulose, methylhydroxy-ethyl cellulose, hydroxypropyl cellulose, hydroxypropyl-methyl cellulose, sodium carboxymethyl cellulose, providone and the polyethylene glycols. The second group consists of the enteric materials that are commonly esters of phthalic acid.

A mix of materials might be used to provide the optimum film coating. Film coating may be carried out in a pan-coater or in a fluidized bed or by compression coating.

Nasal Delivery. Nasal delivery of the agent is also contemplated. Nasal delivery allows the passage of the protein to the blood stream directly after administering the therapeutic product to the nose, without the necessity for deposition of the product in the lung. Formulations for nasal delivery include those with dextran or cyclodextran.

Methods of Treatment, Methods of Preparing a Medicament: In yet another aspect of the present invention, methods of treatment and manufacture of a medicament are provided. Conditions alleviated or modulated by the administration of the present derivatives are those indicated above.

Dosages. For any of the agents, as further studies are conducted, information will emerge regarding appropriate dosage levels for treatment of various conditions in various patients, and the ordinary skilled worker, considering the therapeutic context, age and general health of the recipient, will be able to ascertain proper dosing. Generally, for intravenous injection or infusion, dosage may be lower. The dosing schedule may vary, depending on the circulation half-life, and the formulation used.

The present invention may be better understood by reference to the following non-limiting Examples, which are provided as exemplary of the invention. The following examples are presented in order to more fully illustrate the preferred embodiments of the invention. They should in no way be construed, however, as limiting the broad scope of the invention.

EXAMPLE 1

BIDIRECTIONAL REGULATION OF DARPP-32 PHOSPHORYLATION BY DOPAMINE

Summary

Dopamine has been shown to stimulate phosphorylation of DARPP-32, a phosphoprotein highly enriched in medium-sized spiny neurons of the neostriatum. The contribution of D1-like and D2-like dopamine receptors in the regulation of DARPP-32 phosphorylation has been investigated in mouse striatal slices (see below). Indeed, one aim of the present study was to determine the relative contribution of D1-like and D2-like dopamine receptors to dopamine signaling through the DARPP-32/protein phosphatase-1 cascade, the possible biochemical pathways involved, and the possible effect on this signaling cascade of a widely used antipsychotic drug, raclopride. D1-like and D2-like receptors were found to have opposing effects on the state of DARPP-32 phosphorylation. The D1 receptor agonist SKF82526 increased DARPP-32 phosphorylation. In contrast, the D2 receptor agonist quinpirole decreased basal as well as the D1 agonist-, forskolin-, and 8-bromo-cAMP-stimulated phosphorylation of DARPP-32. In addition, the ability of quinpirole to decrease D1-stimulated DARPP-32 phosphorylation was found to be calcium-dependent and was blocked by the calcineurin inhibitor, cyclosporin A, suggesting that the D2 effect involved an increase in intracellular calcium and activation of calcineurin. In support of this interpretation, $Ca^{2+}$-free/EGTA medium induced a greater than 60-fold increase in DARPP-32 phosphorylation, and abolished the ability of quinpirole to dephosphorylate DARPP-32. The antipsychotic drug raclopride, a selective D2 receptor antagonist, increased phosphorylation of DARPP-32 under basal conditions and in D2 agonist-treated slices. These results demonstrate that dopamine exerts bidirectional control on the state of phosphorylation of DARPP-32.

Materials and Methods

Preparation and incubation of striatal slices. Male C57BL/6 mice (5–8 weeks old) were sacrificed by decapitation. The brains of the decapitated mice were rapidly removed and placed in ice-cold, oxygenated Krebs-$HCO_3$-buffer (124 mM NaCl, 4 mM KCl, 26 mM $NaHCO_3$, 1.5 mM $CaCl_2$, 1.25 mM $KH_2PO_4$, 1.5 mM $MgSO_4$ and 10 mM D-glucose, pH 7.4). Coronal slices (350 $\mu$m) were prepared using a vibratome. Striatum and nucleus accumbens were dissected from the slices in ice-cold Krebs-$HCO_3$- buffer. Each slice was placed in a polypropylene incubation tube with 2 ml of fresh Krebs-$HCO_3$- buffer containing adenosine deaminase (10 $\mu$g/ml). The slices were preincubated at 30° C. under constant oxygenation with 95 % $O_2$/5 % $CO_2$ for 60 minutes. The buffer was replaced with fresh Krebs-$HCO_3$-buffer after 30 minutes of preincubation. In some experiments, slices were incubated in $Ca^{2+}$-free/EGTA medium (124 mM NaCl, 4 mM KCl, 26 mM $NaHCO_3$, 1.25 mM $KH_2PO_4$, 3.0 mM $MgSO_4$, 10 mM D-glucose and I mM EGTA, pH 7.4) for 20 minutes after 60 minutes of preincubation in Krebs-$HCO_3$- buffer. Slices were treated with drugs as specified in each experiment. Drugs were obtained from following sources: Quinpirole, raclopride, SCH23390, NMDA and MK-801 from Research Biochemicals, Inc.; calyculin A, forskolin, and thapsigargin from LC laboratories; 8-bromo-cAMP from Sigma Chemical Co. After the drug treatment, slices were transferred to Eppendorf tubes, frozen on dry ice, and stored at −80° C. until assayed.

Immunoblotting. Frozen tissue samples were sonicated in boiling 1% SDS and boiled for an additional 10 minutes. Small aliquots of the homogenate were retained for protein determination by the BCA protein assay method (Pierce) using bovine serum albumin as a standard. Equal amounts of protein (100 $\mu$g) were loaded onto 12% acrylamide gels, the proteins separated by SDS/PAGE, and transferred to nitrocellulose membranes (0.2 $\mu$m) (Schleicher and Schuell) by the method of Towbin et al. (1979). The membranes were immunoblotted using a monoclonal antibody (mAb-23; 1:750 dilution) [Snyder et al., (1992)], which is a phosphorylation state-specific antibody raised against a DARPP-32 peptide containing phospho-$thr^{34}$, the site phosphorylated by cAMP-dependent protein kinase. A monoclonal antibody (C24-5a; 1:7500 dilution) generated against DARPP-32 (Hemmings and Greengard, 1986), which is not phosphorylation state-specific, was used to estimate the total amount of DARPP-32 in samples. None of the experimental manipulations used in the present study altered the total amount of DARPP-32.

Antibody binding was revealed by incubation with goat anti-mouse horseradish peroxidase-linked IgG (1:6000–8000 dilution) (Pierce) and the ECL immunoblotting detection system (Amersham). Chemiluminescence was detected by autoradiography using DuPont NEN autoradiography film, and phospho-DARPP-32 bands were quantified by densitometry using a Bio-Rad model 620 video densitometer and Bio-Rad 1-D Analyst software.

Data were analyzed by Student's t -test with significance defined as p<0.05.

Results

The effect of dopamine on the level of phosphorylated DARPP-32. Dopamine has been shown to increase the state of phosphorylation of DARPP-32 in rat neostriaturn (Walaas et al., 1983). In this study, the effect of dopamine on DARPP-32 phosphorylation in mouse neostriatal slices was examined using a phosphorylation state-specific antibody which selectively detected phosphorylation at the cAMP-dependent site ($thr^{34}$). $Thr^{34}$-phosphorylated DARPP-32 was detectable in untreated slices. The stoichiometry of DARPP-32 phosphorylation was estimated to be 0.5–1% under basal conditions. Treatment of slices with dopamine (100 $\mu$M) plus the dopamine uptake inhibitor, nomifensine (10 $\mu$M), increased the level of phosphorylated DARPP-32 by 6.64±1.36 fold (P<0.01). DARPP-32 phosphorylation was maximal at 2 to 4 minutes of incubation, and the level of phosphorylated DARPP-32 subsequently decreased (FIG. 1). The total amount of DARPP-32, determined using the DARPP-32 antibody, C24-5a, was similar in each sample.

The phosphorylation state-specific antibody for $thr^{34}$-phosphorylated DARPP-32 also detects the $thr^3$-phosphorylated form of inhibitor-1, a protein phosphatase-1 inhibitor which is closely related structurally and functionally to DARPP-32 [Aitkin et al., (1982); Williams et al., (1986)]. Although detectable levels of inhibitor-1 are expressed in medium-sized spiny neurons of the neostriatum, the level of $thr^{35}$-phosphorylated inhibitor-1 was below the sensitivity of detection in both control and dopamine-treated samples.

Effect of D1 and D2 agonists on the level of phosphorylated DARPP-32: Since both D1-like and D2-like dopamine receptors are expressed in neostriatum, the role of each of these dopamine receptor subclasses in the regulation of DARPP-32 phosphorylation was studied. The D1 agonist SKF82526 (1 $\mu$M) increased the level of phosphorylated DARPP-32 by 5.37±0.99 fold (P<0.01). DARPP-32 phosphorylation was maximal at 5 to 10 minutes of incubation, and the level of phosphorylation subsequently decreased (FIG. 2A). The effect of SKF82526 on DARPP-32 phosphorylation was dose-dependent with a half-maximal effect at about 100 nM, and was abolished by the D1 antagonist SCH23390.

Figure 2B:
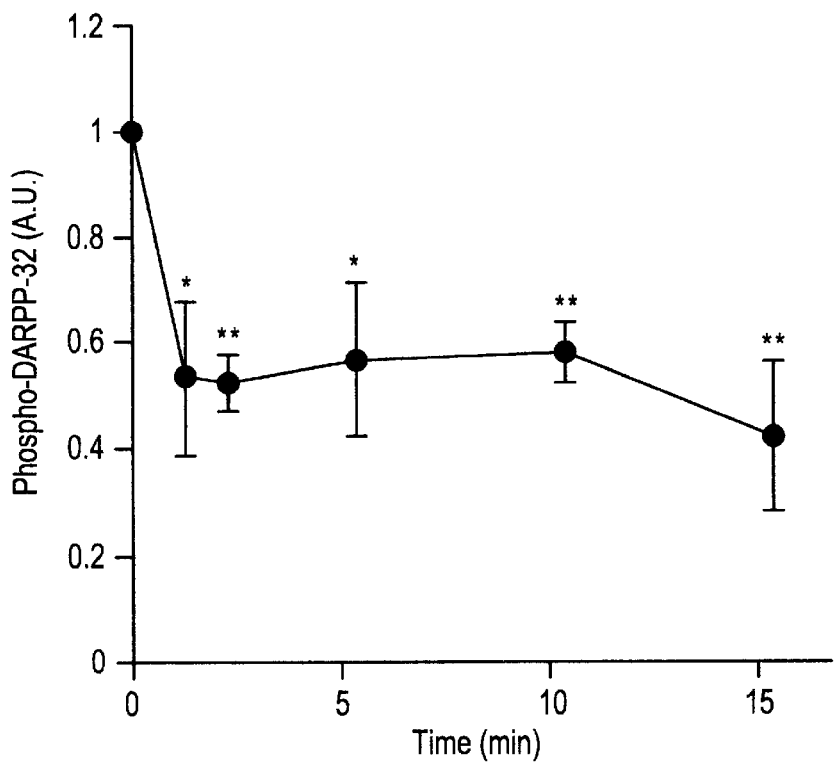
FIG. 2. Effects of a D1 agonist, SKF82526, and a D2 agonist, quinpirole, on the basal level of phosphorylated DARPP-32 in neostriatum.
Figure 3:
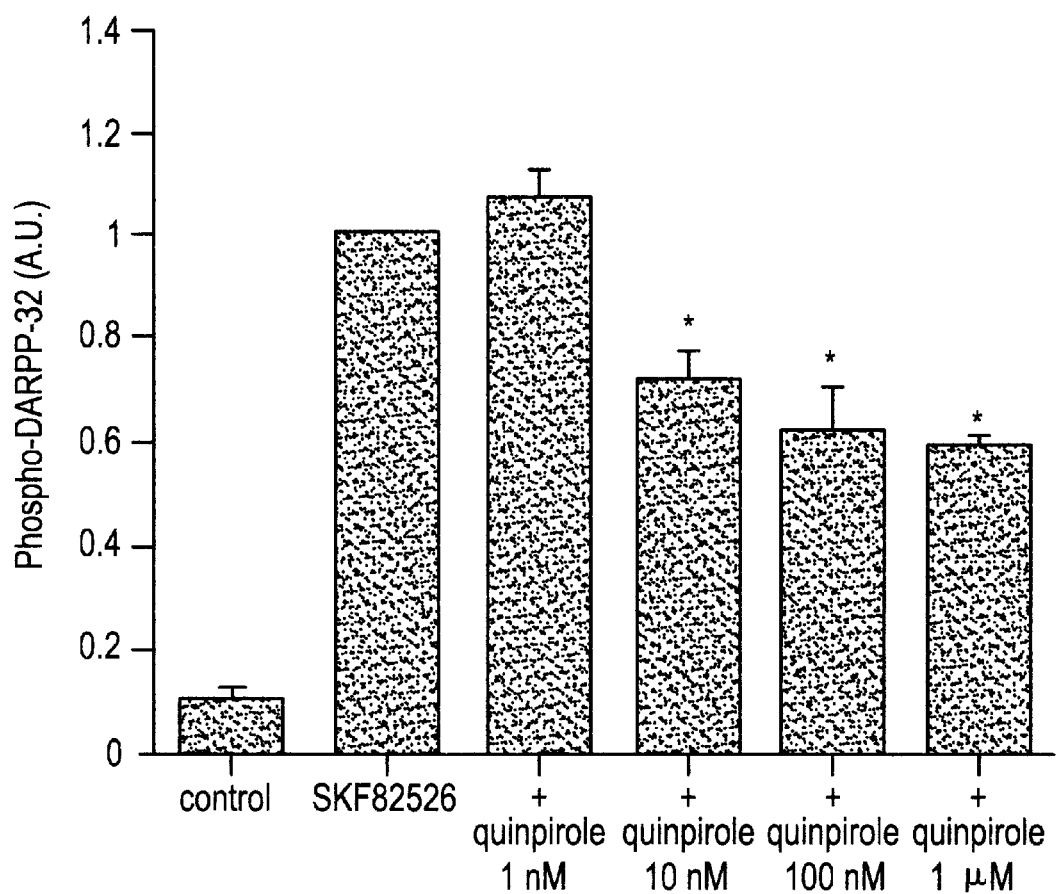
FIG. 3 depicts the opposing effects of a D1 agonist, SKF82526, and a D2 agonist, quinpirole, on the level of phosphorylated DARPP-32 in neostriatum. Slices were preincubated with the indicated concentrations of quinpirole (1 nM to 1 $\mu$M) for 5 minutes and then incubated with quinpirole plus 1 $\mu$M SKF82526 for an additional 5 minutes. The amount of phospho-DARPP-32 was quantitated by densitometry, and the data were normalized to values obtained with SKF82526 alone. Data represent means ±SEM for 4 to 5 experiments. * P<0.01 compared with SKF82526 alone.

Quinpirole (1 $\mu$M), a D2-like receptor agonist, decreased both the basal level (FIG. 2B) and the SKF82526-stimulated level (FIG. 3) of phosphorylated DARPP-32. The effect of quinpirole on the basal level was observed within 1 minute of incubation and was sustained for at least 15 minutes (FIG. 2B). SKF82526 alone increas ed the level of phosphorylated DARPP-32 by 9.36±2.06 fold in this series of experiments, and quinpirole at a concentration of 10 nM to 1 $\mu$M significantly reduced the SKF82526-stimulated DARPP-32 phosphorylation (FIG. 3). A near maximal effect of quinpirole was observed at a concentration of 100 nM, at which concentration phosphorylated DARPP-32 decreased to about 60% of the SKF82526-stimulated level. These results clearly indicate that drugs which activate D1-like and D2-like dopamine receptors have opposing effects on the state of phosphorylation of DARPP-32.

Figure 4A:
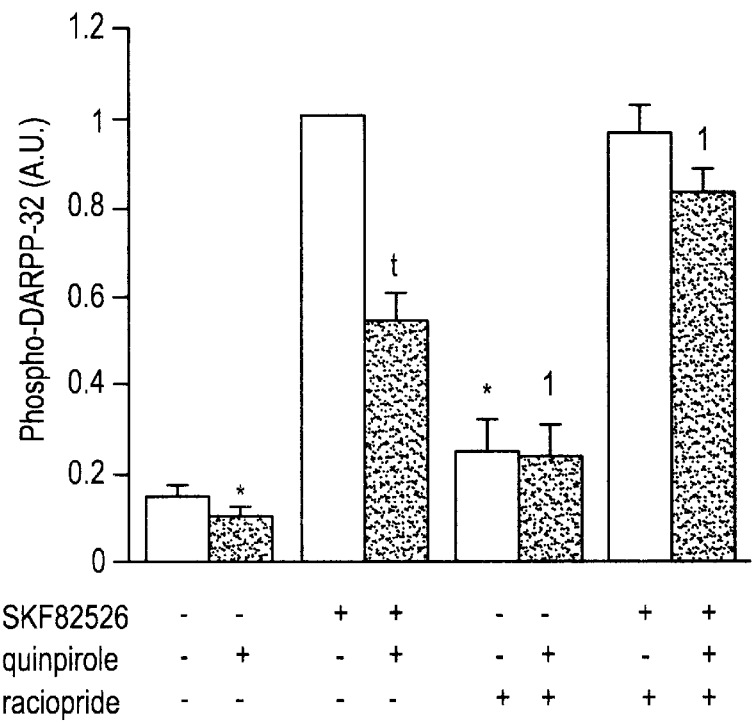
In FIG. 4A the data represent means ±SEM for 6 to 9 experiments. * P<0.01 compared with no addition; †P<0.01 compared with SKF82526 alone; § P<0.05 compared with quinpirole alone; ¶ P<0.01 compared with SKF82526 plus quinpirole.

Effect of the antipsychotic drug raclopride on the level of phosphorylated DARPP-32: Most antipsychotic drugs block D2-like dopamine receptors with potencies proportional to their clinical antipsychotic potencies. The antipsychotic drug raclopride was examined to determine whether it regulated DARPP-32 phosphorylation in neostriatal slices. Raclopride was chosen as the antipsychotic drug of choice because of its potent and selective interaction with D2-like receptors relative to D1-like receptors (Seeman and Van Tol, 1994). Treatment with raclopride (1 $\mu$M) for 20 minutes slightly increased the basal level of phosphorylated DARPP-32 (FIG. 4A), suggesting a tonic activation of D2 receptors under basal conditions. The ability of quinpirole (100 $\mu$M) to decrease the level of phosphorylated DARPP-32 under basal conditions was blocked by raclopride. SKF82526 increased the level of phosphorylated DARPP-32 to a similar extent in the presence and absence of raclopride. However, the ability of quinpirole to decrease the SKF82526-stimulated level of phosphorylated DARPP-32 was dramatically reduced by raclopride. These results indicate that the action of antipsychotic drugs which block D2-like dopamine receptors involves regulation of the state of phosphorylation of DARPP-32.

Figure 4B:
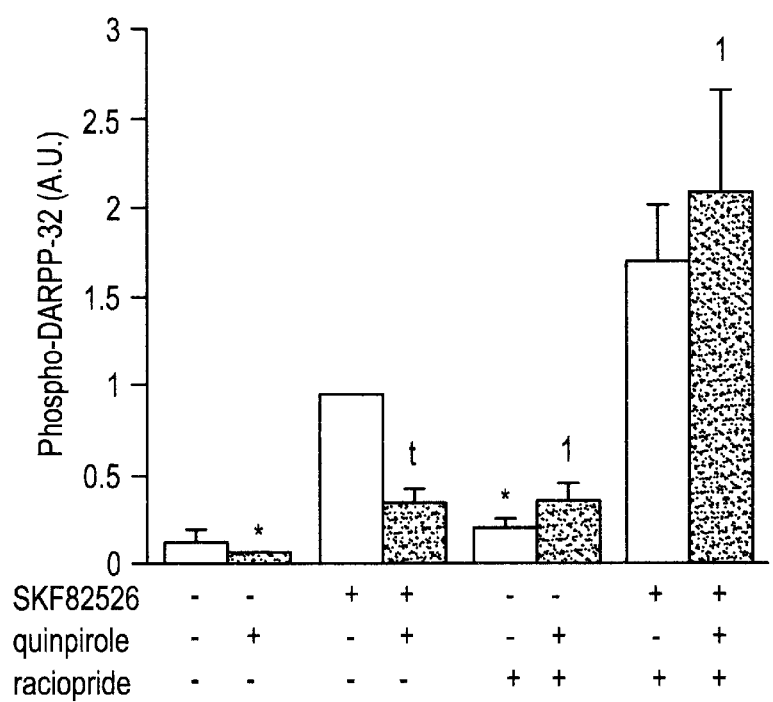
In FIG. 4B data represent means ±SEM for 5 to 7 experiments. * P <0.05 compared with no addition; † P <0.01 compared with SKF82526 alone; § P<0.01 compared with quinpirole alone; ¶ P<0.02 compared with SKF82526 plus quinpirole.

Effects of SKF82526, quinpirole and raclopride, similar to those observed in the neostriatum, were also found in the nucleus accumbens (FIG. 4B). In the nucleus accumbens, SKF82526 increased the level of phosphorylated DARPP-32 by about 7-fold, whereas quinpirole decreased the basal level of DARPP-32 phosphorylation by about 50%. Quinpirole also decreased the SKF82526-stimulated DARPP-32 phosphorylation by about 60%. Raclopride alone induced a small increase in the basal level of phosphorylated DARPP-32. In addition, raclopride abolished the quinpirole-induced decrease in basal DARPP-32 phosphorylation as well as the quinpirole-induced decrease in SKF82526-stimulated DARPP-32 phosphorylation.

Figure 5A:
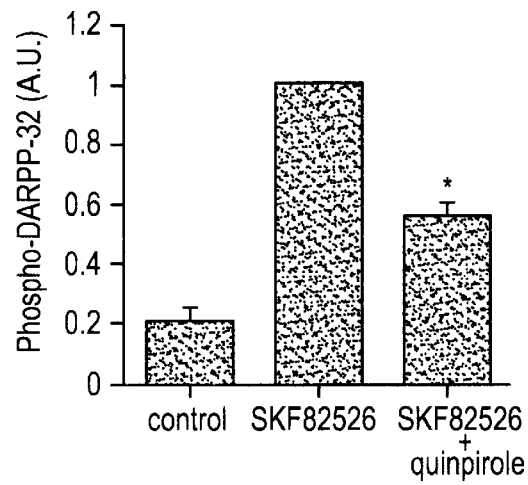
FIG. 5. Effect of a D2 agonist, quinpirole, on stimulated levels of phosphorylated DARPP-32 in neostriatum. Slices were preincubated with quinpirole (1 $\mu$M) for 5 min and then incubated with quinpirole plus either 1 $\mu$M SKF82526, in FIG. 5A, 10 $\mu$M forskolin in FIG. 5B, or 1 mM 8-bromo-cAMP in FIG. 5C for an additional 5 minutes. The amount of phospho-DARPP-32 was quantitated by densitometry, and the data were normalized to values obtained with SKF82526, forskolin or 8-bromo-cAMP alone. Data represent means ±SEM for 3 to 4 experiments. * P<0.01 compared with SKF82526, forskolin or 8-bromo-cAMP alone.
Figure 5B:
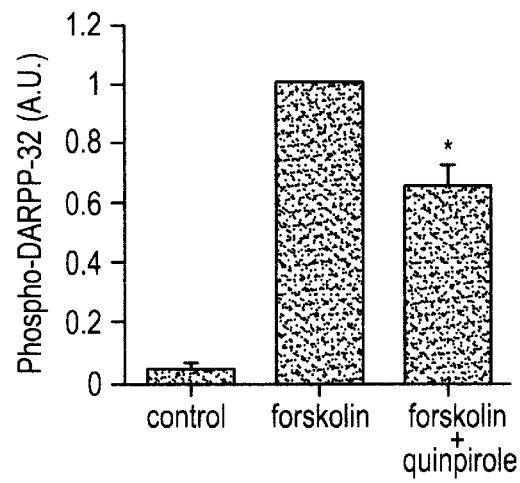
Figure 5C:
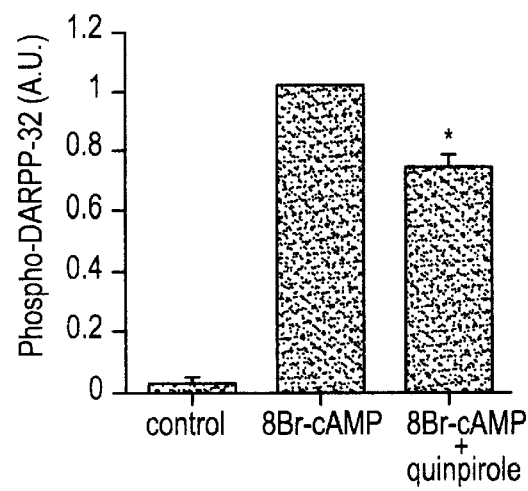

Effect of D2 agonist on stimulated levels of phosphorylated DARPP-32: The ability of the D2 agonist quinpirole to reduce the basal and D1 agonist-stimulated levels of phosphorylated DARPP-32 could be explained in at least two ways (see FIG. 8). Since the activation of D2-like dopamine receptors has been reported to inhibit adenylyl cyclase through a Gi-mediated mechanism, it is possible that D2 receptor agonists decrease DARPP-32 phosphorylation by inhibiting D1 receptor-mediated increases in cAMP formation. Alternatively, activation of D2-like dopamine receptors might increase the activity of calcineurin, a calcium/calmodulin-dependent protein phosphatase, which has been shown to dephosphorylate phospho-DARPP-32 [Halpain et al., (1990); King et al., (1984)]. To evaluate the relative contributions of the cAMP and calcineurin pathways to the regulation of DARPP-32 phosphorylation by a D2 agonist, the ability of quinpirole to regulate DARPP-32 phosphorylation was examined in the presence of forskolin or the cAMP analogue, 8-bromo-cAMP. Treatment of neostriatal slices with forskolin (10 $\mu$M), a direct activator of adenylyl cyclase, increased the level of phosphorylated DARPP-32 by 20-fold after 5 minutes. The D2-like receptor agonist quinpirole (1 $\mu$M) reduced the forskolin-stimulated DARPP-32 phosphorylation by 35 % (FIG. 5), indicating that the effect of quinpirole occurred downstream of the D1 receptor. When neostriatal slices were treated with 8-bromo-cAMP (1 mM) for 5 minutes, the level of phosphorylated DARPP-32 increased by 25-fold and quinpirole (1 $\mu$M) reduced this increase by 30%. This result indicates that the stimulation of D2-like dopamine receptors in striatum decreases DARPP-32 phosphorylation, at least in part, through a mechanism other than inhibition of adenylyl cyclase activity.

Effect of Ca-free/EGTA medium on the level of phosphorylated DARPP-32: Next determined it was determined whether the regulation of DARPP-32 phosphorylation by quinpirole was $Ca^{2+}$-dependent. Incubation of slices in $Ca^{2+}$-free/EGTA medium for 20 minutes increased the level of phosphorylated DARPP-32 by 61.8±10.7 fold (FIG. 6).

The effect of $Ca^{2+}$-free/EGTA medium was much larger than the effect of forskolin or 8-bromo-cAMP. When $Ca^{2+}$-free/EGTA medium was replaced by normal Krebs-$HCO_3$-buffer ($Ca^{2+}$, 1.5 mM), DARPP-32 was dephosphorylated. These results indicate that the phosphorylation of DARPP-32 is tightly regulated by $Ca^{2+}$, and support a role for calcineurin in the regulation of DARPP-32 phosphorylation.

Under $Ca^{2+}$-free conditions (FIG. 7), SKF82526, forskolin and 8-bromo-cAMP each increased the level of phosphorylated DARPP-32, over the already high basal levels, by 1.55±0.12, 2.04±0.22 and 2.42±0.53 fold, respectively. Under each of these conditions, quinpirole failed to decrease the level of phosphorylated DARPP-32. These results further suggest that the effect of D2-like receptor activation is mediated in a $Ca^{2+}$-dependent manner.

The possible involvement of the calcium/calcineurin pathway in the regulation of DARPP-32 phosphorylation was further examined by the use of thapsigargin, which increases intracellular $Ca^{2+}$ levels by inhibition of endoplasmic reticulum $Ca^{2+}$-ATPase (Thastrup et al., 1990). The level of phosphorylated DARPP-32 seen upon incubation of neostriatal slices with SKF82526 (1 $\mu$M) for 5 minutes was reduced by 46.9±7.7% when thapsigargin (5 $\mu$M) was added to the medium 5 min before addition of the D1 agonist. These results suggest that release of $Ca^{2+}$ from intracellular stores can modulate DARPP-32 phosphorylation.

Effect of cyclosporin A on the level of phosphorylated DARPP-32: The effect of cyclosporin A, a specific inhibitor of calcineurin, on the level of phosphorylated DARPP-32 is shown in Table I. Basal levels of phosphorylated DARPP-32 were increased 11–16 fold by cyclosporin A. Moreover, this inhibitor of calcineurin acted synergistically with SKF82526 to increase the level of phosphorylated DARPP-32 and prevented the decrease which occurred upon prolonged incubation of slices with the D1 agonist alone (Table 1A). Although cyclosporin A increased the basal level of phosphorylated DARPP-32 dramatically, a quinpirole-induced decrease in the level of phosphorylated DARPP-32 was still observed in its presence (Table 1B). These results suggest that a D2 agonist-induced decrease in the low, basal level of cAMP contributes to the ability of quinpirole to reduce DARPP-32 phosphorylation. In contrast, cyclosporin A abolished the ability of quinpirole to decrease the SKF82526-stimulated phosphorylation of DARPP-32 (Table 1C). These results indicate that when calcineurin is inhibited in the presence of SKF82526, quinpirole does not reduce the level of cAMP below that sufficient for optimal phosphorylation of DARPP-32.

Effect of D2 agonist on the level of phosphorylated DARPP-32 is not mediated through the NMDA receptor: The activation of NMDA receptors decreases the phosphorylation of DARPP-32 in the neostriatum (Halpain et al., 1990). This effect has been hypothesized to occur through a mechanism involving increased intracellular calcium and activation of calcineurin. The D2-mediated regulation of DARPP-32 phosphorylation was examined to determine whether it requires the activation of NMDA receptors. Although both NMDA and quinpirole antagonized the ability of SKF82526 to increase the level of phosphorylated DARPP-32, the effect of NMDA, but not that of quinpirole, was abolished by the NMDA receptor antagonist MK801 (Table 2). These results indicate that the ability of quinpirole to decrease the level of phosphorylated DARPP-32 occurs independently of the NMDA receptor. Treatment with MK801 increased the level of phosphorylated DARPP-32 under basal conditions, suggesting that, in our preparation, the NMDA receptor is tonically active and dephosphorylates DARPP-32 through activation of calcineurin.

TABLE 1

Effect of cyclosporin A on the level of phospho-DARPP-32 in neostriatum

|  | Cyclosproin A (−) | Cyclosporin A (+) |
| --- | --- | --- |
| A. D1 agonist SKF82526 |  |  |
| 0 min | 1.00 | 16.0 ± 1.6* |
| 5 min | 7.14 ± 0.97* | 31.6 ± 2.8** |
| 30 min | 3.07 ± 0.66*,*** | 28.0 ± 3.1** |
| B. D2 agonist quinpirole |  |  |
| 0 min | 1.00 | 13.50 ± 1.74* |
| 2 min | 0.525 ± 0.051* | 5.98 ± 1.28** |
| 10 min | 0.580 ± 0.058* | 5.60 ± 1.05** |
| C. D1 + D2 agonist |  |  |
| Control | 1.00 | 11.0 ± 2.5* |
| SKF82526 | 10.61 ± 2.28* | 21.1 ± 2.3** |
| SKF82526 + quinpirole | 4.78 ± 1.20*,*** | 20.3 ± 2.5** |

Slices were preincubated in the absence or presence of cyclosporin A (CyA) (5 μm) for 60 min, followed by the addition of SKP82526 and/or quinpirole. The amount of phospho-DARPP-32 was quantitated by densitometry, and the data were normalized to values obtained with control.
A. Slices were incubated with SKF82526 (1 μm) for the indicated times. Data represent means ± SEM for five to nine experiments.
*p < 0.01 compared with 0 min/CyA (−); p < 0.01 compared with 0 min/CyA (+); *p < 0.01 compared with 5 min/CyA (−).
B. Slices were incubated with quinpirole (1 μm) for the indicated times. Data represents means ± SEM for five to seven experiments.
*p < 0.01 compared with 0 min/CyA (−); **p < 0.01 compared with 0 min/CyA (+).
C. Slices were preincubated with quinpirole (1 μm) for 5 min and then incubated with quinpirole plus SKF82526 (1 μm) for an additional 5 min. Data represent means ± SEM for six to nine experiments.
*p < 0.01 compared with control/CyA (−); p < 0.01 compared with control/CyA (+); *p < 0.05 comparedwith SKF82526/CyA (−).

Effect of D2 agonist on the level of phosphorylated DARPP-32 is not reduced by tetrodotoxin: It seemed possible that the D2-mediated decrease in DARPP-32 phosphorylation might involve release of a neurotransmitter from neurons other than those containing D1 receptors. The effect of tetrodotoxin (TTX) on the ability of quinpirole to affect DARPP-32 phosphorylation was therefore examined, since TTX is an inhibitor of sodium-dependent action potentials. TTX failed to reduce the effect of quinpirole (Table 3), whereas it increased the levels of phosphorylated DARPP-32 both under basal conditions and in the presence of SKF 82526. The effect of TTX, like that of MK-801, supports the possibility that, in our preparation, the NMDA receptor is tonically active and dephosphorylates DARPP-32 through activation of calcineurin. The data provide no support for the possibility that quinpirole achieved its effect by release of a neurotransmitter from interneurons.

TABLE 2

Effect of D2 agonist on the level of phospho-DARPP-32 is not mediated through the NMDA receptor

|  | MK801 (−) | MK801 (+) |
| --- | --- | --- |
| Control | 0.103 ± 0.021* | 0.247 ± 0.044** |
| SKF82526 | 1.000 | 1.115 ± 0.078 |
| SKF82526 ± NMDA | 0.042 ± 0.009* | 1.042 ± 0.085 |
| SKF82526 ± quinpirole | 0.598 ± 0.137* | 0.616 ± 0.084*** |

Neostriatal slices were incubated for a total of 20 min in the absence or presence of the NMDA receptor antagonist MK801 (100 μm). MK801 was added at 0 min, NMDA (100 μm) or quinpirole (1 μm) at 10 min, and SKF82526 (1 μm) at 15 min of incubation.
The amount of phospho-DARPP-32 was quantitated by densitometry, and the data were normalized to values obtained with SKF82526 alone. Data represent means ± SEM for four to seven experiments.
*p <0.01 compared with SKF82526/MK801 (−); p < 0.05 compared with control/MK801 (−); *p < 0.01 compared with SKF82526/MK801 (+).

TABLE 3

Effect of D2 agonist on the level of phospho-DARPP-32 is not reduced by tetrodotoxin (TTX)

|  | TTX (−) | TTX (+) |
| --- | --- | --- |
| Control | 0.686 ± 0.109 | 1.000* |
| SKF82526 | 3.282 ± 0.575** | 5.492 ± 0.780***,**** |
| SKF82526 ± quinpirole | 1.716 ± 0.409*,*** | 1.968 ± 0.559***** |

Neostriatal slices were incubated for a total of 20 min in the absence or presence of TTX (1 μm). TTX was added at 0 min, quinpirole (1 μm) at 10 min, and SKF82526 (1 μm) at 15 min of incubation. The mount of phospho-DARPP-32 was quantitated by densitometry, and the data were normalized to values obtained with TTX alone. Data represent means ± SEM for six to seven experiments.
**p < 0.01, *p < 0.05 compared with control/TTX (−); *p < 0.05 compared with SKF82526/TTX (−); p < 0.01 compared with control/TTX (+); ***p < 0.01 compared with SKF82526/TTX (+).

Discussion

Adenylyl cyclase activity in the neostriatum is regulated through the opposing interactions of D1 and D2 receptors (Stoof and Kebabian, 1981). The inhibition of adenylyl cyclase activity by D2 receptors almost certainly contributes to the ability of quinpirole to reduce the phosphorylation of DARPP-32. However, such a mechanism does not fully explain the results of the present study since the activation of D2 receptors effectively decreases DARPP-32 phosphorylation induced by an exogenous cAMP analog, 8-bromo-cAMP. These data clearly indicate that a cAMP-independent pathway also participates in D2-receptor mediated regulation of DARPP-32.

Figure 8:
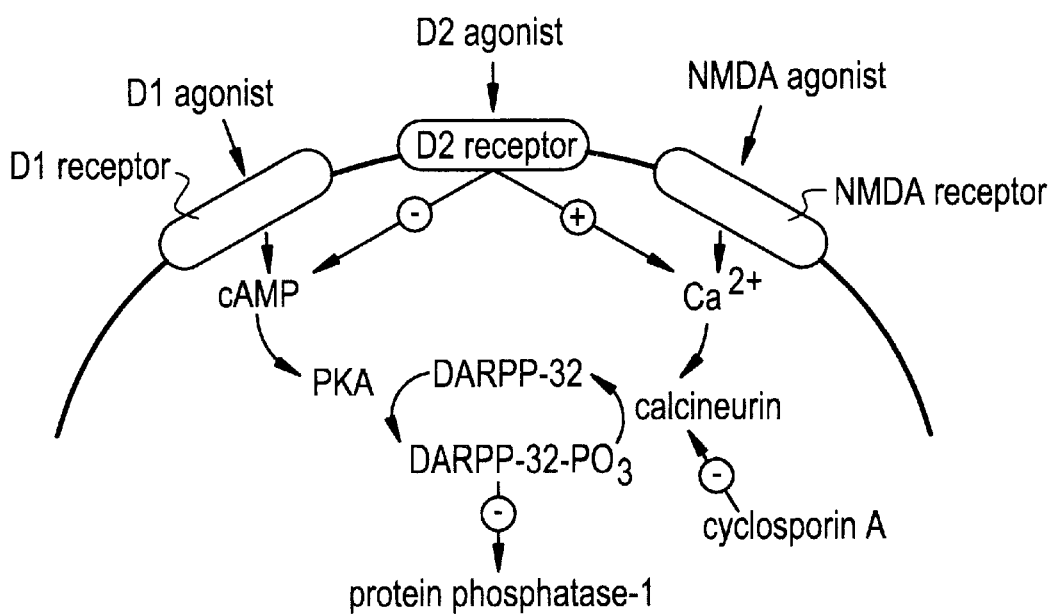
FIG. 8. Postulated pathways by which dopamine may regulate DARPP-32 phosphorylation. Activation of dopamine D1 receptors increases cAMP, leading to the activation of PKA and the phosphorylation of DARPP-32 on $thr^{34}$, converting it into a potent inhibitor of protein phosphatase-1. Activation of dopamine D2 receptors decreases DARPP-32 phosphorylation by two mechanisms (which might occur in the same or in different groups of neurons): one involves an inhibition of adenylyl cyclase, a decrease in cAMP, a decrease in activity of PKA and a decreased phosphorylation of DARPP-32; the other involves an increase in intracellular $Ca^{2+}$, an activation of calcineurin and an increased dephosphorylation of thr-phospho-DARPP-32. This scheme is supported by evidence showing that NMDA receptor activation (Halpain et al., 1990) and thapsigargin (below), both of which raise intracellular $Ca^{2+}$, cause the dephosphorylation of $thr^{34}$-phospho-DARPP-32.

One such mechanism by which quinpirole reduces the phosphorylation of DARPP-32 is through an increase in the activity of a protein phosphatase(s) which dephosphorylates thr$^{34}$ on DARPP-32 The calcium/calmodulin-dependent protein phosphatase, calcineurin, has been shown to dephosphorylate DARPP-32 with a high efficiency in vitro (King et al., 1984). The present study demonstrates that the ability of a D2 receptor agonist to reduce D1-stimulated DARPP-32 phosphorylation is blocked by the calcineurin inhibitor, cyclosporin A. The data indicate that the activation of D2 receptors induces an increase in intracellular calcium and an activation of calcineurin in neostriatal neurons, leading to dephosphorylation of DARPP-32. It seems likely then that D2 agonists cause the dephosphorylation of DARPP-32 both by reducing PKA-stimulated phosphorylation [e.g., Table 1B, cyclosporin A (+)] and by increasing calcineurin-stimulated dephosphorylation [e.g., FIG. 5C]. These dual effects of D2 receptor activation on DARPP-32 phosphorylation are shown in FIG. 8.

Calcium omission induced a dramatic increase in the level of phosphorylated DARPP-32 in neostriatal slices and blocked D2-mediated inhibition of DARPP-32 phosphorylation, further supporting a role for the calcium-dependent phosphatase in DARPP-32 regulation. Calcium omission increased DARPP-32 phosphorylation much more than did cyclosporin A treatment. This difference in effectiveness might be due to incomplete inhibition of calcineurin by cyclosporin A. Alternatively, other calcium-dependent processes could also contribute to the regulation of DARPP-32 phosphorylation. For instance, a major subtype of adenylyl cyclase, type V calcium-inhibitable adenylyl cyclase, is enriched in neostriatum (Cooper et al., 1995) and calcium omission would be expected to increase the activity of this enzyme, resulting in a potentiation of D1-stimulated DARPP-32 phosphorylation. In addition, the degradation of cAMP in neostriatum is mediated by a calcium-dependent phosphodiesterase activity (Polli and Kincaid, 1994) which would be anticipated to decrease under conditions of low calcium availability, leading to an additional mechanism for the potentiation of D1-stimulated DARPP-32 phosphorylation. Thus, physiological conditions which reduce intracellular calcium would be expected to decrease the driving force for calcium-dependent dephosphorylation and may also affect multiple signaling enzymes within neostriatal neurons to promote cAMP-dependent phosphorylation of DARPP-32 by PKA.

Recent studies have shown that multiple effectors including potassium channels, calcium channels, and phospholipase C can be regulated by G-protein-mediated interactions with D2 receptors (Huff, 1996). The functional interaction of the D2 receptor with these effectors varies with the host cells and tissues which have been studied. For example, Yan and colleagues (1996) have reported that D2 receptors on neostriatal neurons inhibit calcium channel conductances through interaction with a $G_{I/o}$ class protein. Valler et al. (1990) have reported that D2 receptors expressed in pituitary GH4C1 cells decrease intracellular $Ca^{2+}$ by inhibiting calcium channel activity, and that, in contrast, D2 receptors expressed in Ltk- fibroblasts increase intracellular $Ca^{2+}$ by activating phospholipase C. A similar heterogeneity in D2 receptor effects on ion channel activity has been shown in neostriatal neurons by Surmeier et al. (1992), who demonstrated that D2 receptors could decrease sodium current in medium spiny neurons through a membrane-delimited pathway and increase it through a soluble second messenger pathway.

The present results indicate that the effect of D2 receptors on DARPP-32 phosphorylation is calcium-dependent and mediated by an increase in intracellular $Ca^{2+}$ and an activation of calcineurin. It is possible that D2 receptors located on DARPP-32-containing neostriatal neurons directly mediate an increase in intracellular $Ca^{2+}$ either through regulation of potassium channels, calcium channels or phospholipase C. The contributions of these various signal transduction pathways to the regulation of intracellular Ca2+, calcineurin activity and DARPP-32 phosphorylation remain to be clarified. In addition, the data do not exclude the possibility that other D2-like receptors, including the D3 and D4 receptors, which are expressed in medium spiny neurons, albeit at low density (Surmeier et al., 1996), also contribute to signaling pathways responsible for calcineurin-dependent dephosphorylation of DARPP-32.

In principle, the effect of D2 agonists in causing the dephosphorylation of DARPP-32 might be attributable either to a direct effect on D1 receptor-containing neurons or to an indirect effect involving release of neurotransmitter from other neurons. In support of a direct action, Surmeier et al. (1996) have reported that as many as 60% of the neostriatal neurons that contain D1-class receptors also contain D2-class receptors. The present data, indicating that quinpirole induces a 40% decrease in SKF 82526-induced phosphorylation of DARPP-32, is consistent with a limited expression of D2- class receptors in D1 receptor-containing neurons. Activation of NMDA receptors which are ubiquitous on medium spiny neurons (Ghasernzadeh et al., 1996) induces a 100% decrease in SKF-induced phosphorylation of DARPP-32 (Table 2). Thus, the difference in the distribution of D2 and NMDA receptors may explain the greater efficacy of NMDA in reducing D1-stimulation of DARPP-32 phosphorylation.

Some groups have reported a very low degree of overlap of the two receptor classes [Gerfen et al., (1990); Hersch et al., (1995)]. Specifically, they report an apparent complete segregation of D1 and D2 receptors on dendrites (Hersch et al., 1995) with the possibility of up to a 20% co-localization of D1 and D2 receptors on neostriatal somata (Hersch et al., 1995). The results of these latter investigators would argue for an indirect mechanism for the action of quinpirole, involving the release, from non-D1 receptor-containing neurons, of a neurotransmitter which, in turn, induces calcium-dependent activation of calcineurin and mediates DARPP-32 dephosphorylation in medium-sized spiny neurons. A similar mechanism has been proposed for the dephosphorylation of phospho-thr$^{34}$-DARPP-32 in neostriatal neurons by the neuropeptide cholecystokinin (CCK) (Snyder et al., 1993). CCK-mediated decreases in DARPP-32 phosphorylation are blocked by the NMDA receptor antagonist, MK801, suggesting that CCK regulates DARPP-32 by release of excitatory amino acids like glutamate and aspartate from either corticostriatal nerve terminals or interneurons. The D2-mediated release of a neurotransmitter from interneurons seems unlikely to be involved in the D2-mediated decrease in DARPP-32 phosphorylation, since tetrodotoxin, an inhibitor of sodium-dependent action potentials, did not block the D2 agonist effect (Table 3).

In addition, the present study indicates that although the activation of NMDA receptors, like that of D2 receptors, decreases basal and D1-stimulated DARPP-32 phosphorylation in neostriatal slices through stimulation of calcineurin, these effects are independent, since the D2 receptor effect was not blocked by MK801, an NMDA receptor antagonist.

EXAMPLE 2

PREPULSE INHIBITION STUDIES IN MICE AFTER ADMINISTRATION OF CALCINEURIN INHIBITORS

Introduction

Dopamine is an important neurotransmitter in the brain. It regulates many basic neuronal functions including motor control, hormonal secretion, motivation and various aspects of cognition. Dopamine is released at presynaptic terminals and functions by binding to post-synaptic dopamine receptors on the cell surface of so called "dopaminoceptive" neurons. Dopaminoceptive neurons are found concentrated in particular regions of the brain most notably the striatum, cortex and hypothalamus. There are five known dopamine receptors which can be grouped into two main classes: D1-like and D2-like. The binding of dopamine to the various dopamine receptors initiates changes in various signal transduction pathways in the post-synaptic neuron. These signal transduction pathways act to change the excitability of the neuron by altering the activity of various ion channels and ion pumps such as calcium channels, sodium channels and the $Na^+/K^+$ ATPase. The way such pathways are regulated by dopamine normally and how they are altered in various diseases such as Parkinson's disease, schizophrenia, and drug addiction is only beginning to be understood.

Research by Greengard and colleagues has shown that protein phosphorylation mechanisms play a prominent role in the regulation of dopamine signal transduction. Specifically, it has been shown that dopamine binding to the D1 receptor activates adenylyl cyclase leading to increases in the level of cAMP. This leads to the activation of protein kinase A and the subsequent phosphorylation of a protein referred to as DARPP-32 (for dopamine and cyclic AMP regulated phosphoprotein). The phosphorylation of DARPP-32 occurs on threonine-34 converting, it into a potent inhibitor of protein phosphatase-1. This inhibition of protein phosphatase-1 alters the phosphorylation of various downstream effectors such as N-/P-type calcium channels and the $Na^+/K^+$ ATPase leading to alterations in neuronal activity.

Figure 9:
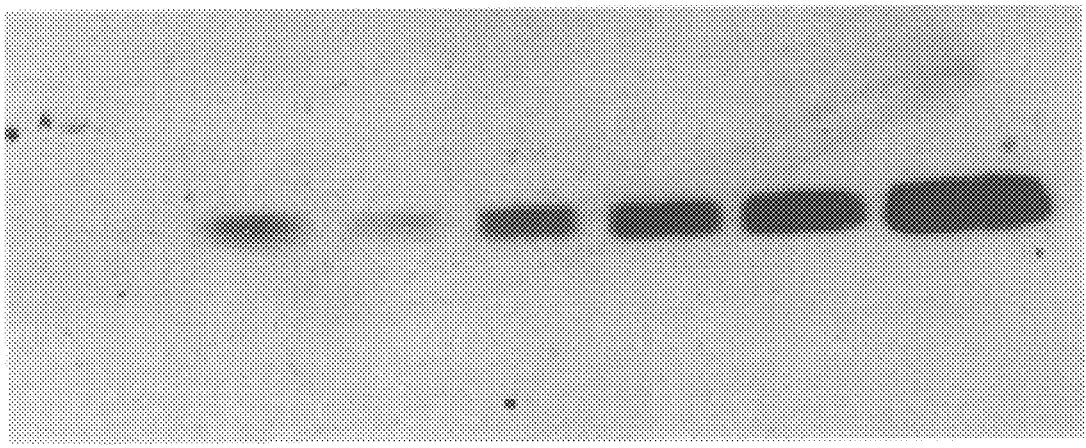
FIG. 9. FK506 increases the level of DARPP-32 phosphorylation in neostriatal slices. Rat neostriatal slices were incubated in the absence (control) or presence of forskolin (10 $\mu M$) alone; or forskolin and FK506 using the various concentrations shown. The results demonstrate that inhibition of calcineurin activity by FK506 increases DARPP-32 phosphorylation in a dose-dependent manner.

As shown in Example 1, above, DARPP-32 phosphorylation is regulated not only by D1 receptor activation but also by the D2 receptor. Thus Example 1 demonstrates that activation of the D2 receptor strongly reduces both the basal level of DARPP-32 phosphorylation and phosphorylation stimulated by D1 agonists (FIG. 3). This decrease in DARPP-32 phosphorylation occurs via the activation of the protein phosphatase calcineurin. Data in Table 1 demonstrate that inhibition of the phosphatase calcineurin using, the drug cyclosporin A, raises the phosphorylation state of DARPP-32. Cyclosporin A also prevents the D2-mediated decrease in DARPP-32 phosphorylation. In addition another inhibitor of calcineurin, FK506 [Schreiber et al., Science, 253:283–287 (1991); Dawson, Ann. of Neur. 40:559–560 (1996)] also raises the level of DARPP-32 phosphorylation (FIG. 9).

Figure 10:
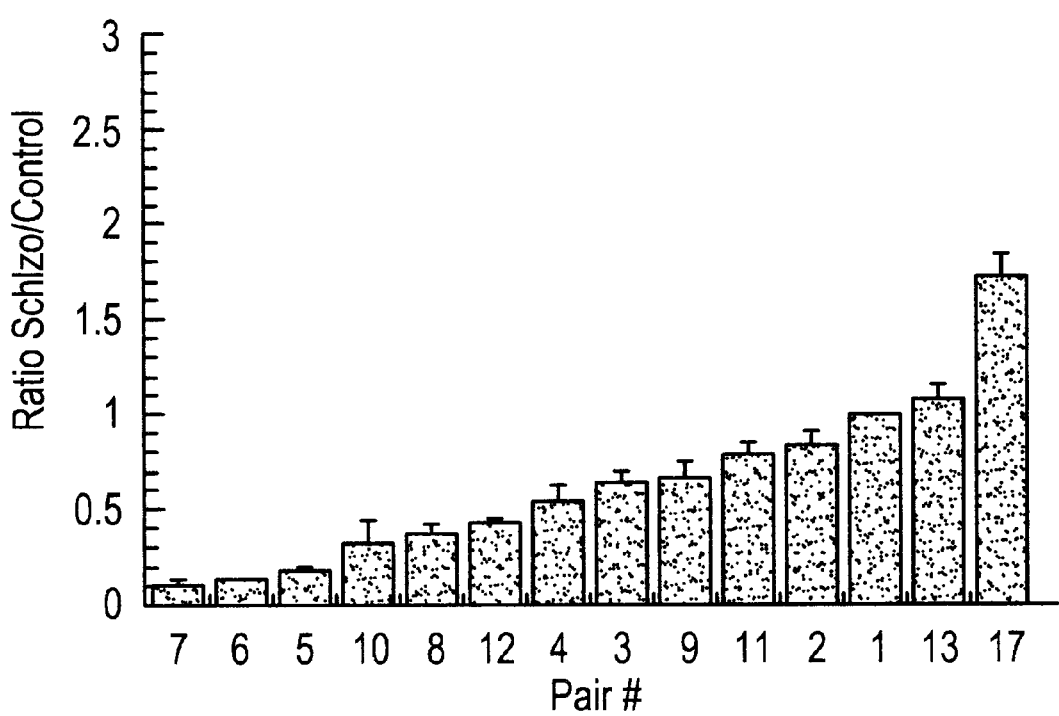
FIG. 10 depicts a plot of the ratio of DARPP-32 levels (in the dorsilateral prefrontal cortex) of post-mortem samples from brains of schizophrenics divided by the matched control brains. Pair numbers refer to the particular schizophrenic patient compared to its matched non-schizophrenic control. Levels of DARPP-32 were determined by immunoblotting.

Example 1 also demonstrates that raclopride, a widely used antipsychotic, increases the phosphorylation of DARPP-32. Such a finding suggests that antipsychotic drugs may act by increasing DARPP-32 phosphorylation. Additional data also supports this premise: (1) Studies examining the level of DARPP-32 in post-mortem samples from 14 schizophrenic patients along with their age, gender and autolysis time-matched controls have shown significant decreases in DARPP-32 in the dorsolateral prefrontal cortex of schizophrenic patients relative to the controls (FIG. 10). These data suggest that the reduction of DARPP-32 phosphorylation and the consequential regulation of protein phosphatase-1 that DARPP-32 phosphorylation provides is intimately related to the pathophysiology of schizophrenia. (2) A recent report has demonstrated that treatment with a D1 antagonist not only fails to ameliorate the symptoms of schizophrenia but actually intensifies these symptoms (Karlsson et al., 1995). D1 antagonists, like D2 agonists would be expected to inhibit increases in DARPP-32 phosphorylation.

The above studies indicate that lowered levels of DARPP-32 phosphorylation correlate with the schizophrenic state and that drugs that can act to raise DARPP-32 phosphorylation could relieve the symptoms of schizophrenia as well as other diseases of dopamine dysregulation such as Parkinson's disease, Tourette's syndrome, drug abuse and attention deficit disorder. As demonstrated in Example 1 and FIG. 9, drugs such as cyclosporin and FK506 can act to raise the level of DARPP-32 phosphorylation and thus can act in the treatment of schizophrenia.

Materials and Methods

Chambers that are used to assess startle are housed in a sound-attenuated room with a 60 dB(A) ambient noise level. Such chambers consist of a Plexiglass cylinder 8.2 cm in diameter resting on a 12.5×25.5 cm Plexiglass frame within a ventilated enclosure. Acoustic noise bursts are presented via a speaker mounted 24 cm above the animal. A piezoelectric accelerometer mounted below the Plexiglass frame detects and transduces motion within the cylinder. The delivery of acoustic stimuli is controlled by a microcomputer. Startle amplitude is defined as the average of 100 readings. Background noise and all acoustic stimuli are delivered through a speaker (frequency response between 0.5 and 16 Khz) in a chamber. The test session consists of giving: (i) a startle stimulus alone (a 118 dB [A] 40 ms broad band burst); or (ii) no stimulation; or (iii) a startle stimulus preceded 100 ms earlier by a prepulse (a 70 dB [A] 20 ms broad band burst). The amount of PPI is expressed as the percentage decrease in the startle response caused by the presentation of the prepulse. The amount of PPI is calculated using the following equation: [(startle amplitude caused by pulse alone minus startle amplitude caused by pulse preceded by prepulse)/(startle amplitude caused by pulse alone)]×100.

FK506 is available from Fujisawa Pharmaceuticals. The DARPP-32 knockout mice were prepared as described in U.S. Patent Application 08/649,103 filed on May 17, 1996 hereby incorporated by reference in its entirety.

Results

Prepulse inhibition to startle in the DARPP-32 knockout and using FK506: Prepulse inhibition (PPI) of the startle reflex refers to the reduction of the startle response due to the prior presentation of a stimulus that is below startle threshold. This effect is presumed to reflect sensorimotor gating mechanisms (Braff and Geyer, 1990). PPI is of particular interest to clinical researchers because it is deficient in schizophrenia [Braff et al., (1992); Grillon et al., (1992)]. Theoretically, a disturbance in such gating mechanisms may permit the intrusion of unwanted sensory information, behaviors or thoughts into ongoing behavioral patterns and may manifest itself as clinical syndromes (Swerdlow et al., 1993). PPI is disrupted in rodents by treatment with agonists for D2 receptors [Yan et al., (1996); Geyer and Swerdlow, 1994).

PPI in the DARPP-32 knockout: Preliminary studies measuring PPI in mice containing a genetic deletion of the DARPP-32 gene demonstrate that using a 12dB prepulse and a tactile startle paradigm that PPI is diminished in the DARPP-32 knockout mouse. These studies illustrate that mice lacking DARPP-32 show a reduction in a behavior that is also reduced in schizophrenics.

PPI in response to FK506 : FK506 is chosen in these studies because it has been shown that cyclosporin fails to cross the blood-brain barrier effectively (Begley et al., 1990) whereas FK506 effectively crosses the blood-brain barrier. PPI is measured in mice after the following drug treatments: (1) no treatment; (2) after administration of a D2 agonist, such as quinpirole (0–1.0 mg/Kg subcantaneously); (3) after administration of D2 agonist and FK506 concurrently (FK506 is administered intravenously in doses ranging from 1 to 1000 nM); (4) after administration of FK506 alone. These studies demonstrate that quinpirole reduces the degree of PPI and that FK506 blocks the reduction of PPI mediated by quinpirole. In addition FK506 alone can increase the degree of PPI.

Discussion

In view of the pharmacology of PPI the results described herein are consistent with a correlation of schizophrenia and the effect of dopamine agonists on DARPP-32 phosphorylation. D2 agonists are known to lower the degree of PPI and lower the level of DARPP-32 phosphorylation. Schizophrenics are known to have reduced PPI. Therefore these results illustrate that the administration of FK506 to an animal model in an accepted paradigm for schizophrenia can reverse the effects of a drug that induces a behavioral state found in schizophrenics.

Various publications are cited herein including those below, the disclosures of which are incorporated by reference in their entireties.

References

Aitkin A, Bilhaim T, Cohen P (1982) Complete primary structure of protein phosphatase inhibitor-1 from rabbit skeletal muscle. Eur J Biochem 126: 235–246.

Anden N E, Carlsson A, Dahlstrom A, Fuxe K, Hillarp N A, Larsson K (1964) Demonstrating and mapping out of nigroneostriatal dopamine neurons. Life Science 3: 523–530.

Aperia A, Fryckstedt J, Svensson L-B, Hemmings Jr H C, Naim A C, Greengard P (1991) Phosphorylated Mr 32,000 dopamine- and cAMP-regulated phosphoprotein inhibits Na+,K+-ATPase activity in renal tubule cells. Proc Natl Acad Sci, USA 88: 2798–2801.

Begley D. J. et al. (1990) J. of Neurochem. 55:1222–1230.

Braff, D. L., and Geyer, M. A. (1990) Sensorimotor gating and schizophrenia: human and animal model studies. Arch Gen Psychiatry 47:181–188.

Braff, D. L., Grillon, C., and Geyer, M. A. (1992) Gating and habituation of the startle reflex in schizophrenic patients. Arch Gen Psychiatry 49, 206–215.

Cooper D M, Mons N, Karpen J W (1995) Adenylyl cyclases and the interaction between calcium and cAMP signaling. Nature 374: 421–424.

Davis K L, Kahn R S, Ko G, Davidson M (1991) Dopamine in schizophrenia: A review and reconceptualization. Amer J Psychiat 148, 1474–1486.

Dawson et al., (1993) Proc. Natl. Acad. Sci. 90:9808–9812.

Dragunow M, Robertson G S, Faull R L, Robertson H A, Jansen K (1990) D2 dopamine receptor antagonists induce fos and related proteins in rat striatal neurons. Neuroscience 37: 287–94.

Fitzgerald L W, Deutch A Y, Gasic G, Heinemann S F, Nestler E J (1995) Regulation of cortical and subcortical glutamate receptor subunit expression by antipsychotic drugs. J Neurosci 15: 2453–61.

Gerfen C R, Engber T M, Mahan L C, Susel Z, Chase T M, Monsma Jr F J, Sibley D R (1990) D1 and D2 dopamine receptor-regulated gene expression of striatonigral and striatopallidal neurons. Science 250: 1429–1432.

Geyer M. A. and Swerdlow, N. R. (1994) Pharmacol. Biochem. and Behav. 49:155–163.

Ghasemzadeh M B, Sharma S, Surmeier D J, Ebenvine J H, Chesselet M-F (1996) Multiplicity of glutamate receptor subunits in single striatal neurons: An RNA amplification study. Molec Pharmacol 49: 852–859.

Grillon, C., Ameli, R., Charney, D. S., Krystal, J., and Braff, D. L. (1992). Startle gating deficits occur across prepulse intensities in schizophrenic patients. Biol. Psychiatry 32:939–943.

Halpain S, Girault J-A, Greengard P (1990) Activation of NMDA receptors induced dephosphorylation of DARPP-32 in rat striatal slices. Nature 343: 369–372.

Hemmings Jr H C, Greengard P, Tung H Y L, Cohen P (1984) DARPP-32. a dopamine-regulated neuronal phosphoprotein, is a potent inhibitor of protein phosphatase-1. Nature 310: 503–505.

Hemmings Jr H C, Greengard P (1986) DARPP-32, a dopamine- and adenosine 3':5'-monophosphate-regulated phosphoprotein: regional, tissue, and phylogenetic distribution. J Neurosci 6: 1469–1481.

Hersch S M, Ciliax B J, Gutekunst C A, Rees H D, Heilman C J, Yung K K, Bolarn J P, Ince E, Yi H, Levey A I (1995) Electron microscopic analysis of D1 and D2 dopamine receptor proteins in the dorsal striatum and their synaptic relationships with motor corticostriatal afferents. J Neurosci 15: 5222–37.

Huff R M (1996) Signal transduction pathways modulated by the D2 subfamily of dopamine receptors. Cell Signal 8: 453–459.

Jackson D M, Westlind-Danielsson A (1994) Dopamine receptors: molecular biology, biochemistry and behavioral aspects. Pharmac Ther 64: 291–370.

Karlsson P, Smith L, Farde L, Harnryd C, Sedvall G, Wiesel F A (1995) Lack of apparent antipsychotic effect of the D1-dopamine receptor antagonist SCH39166 in acutely ill schizophrenic patients. Psychopharmacology 121: 309–16.

King M M, Huang C Y, Chock P B, Nairn A C, Hemmings Jr H C, Chan K-FJ, Greengard P (1984) Mammalian brain phosphoproteins as substrates for calcineurin. J Biol Chem 259: 8080–8083.

Levey A I, Hersch S M, Rye D B, Sunahara R K, Niznik N B, Kitt C A, Price D L, Maggio R, Brann M R, Ciliax B J (1993) Localization of D1 and D2 dopamine receptors in brain with subtype-specific antibodies. Proc Natl Acad Sci, USA 90: 8861–8865.

Nishi A, Snyder G L, Fienberg A, Allen P, Fisone G, Nairn A C, Aperia A, Greengard P. (1996) Role of DARPP-32 in the regulation of Na+,K+-ATPase activity in striatal neurons. Soc. Neurosci. Abst. 26: 380.

Onali P, Olianas M C, and Gessa G L (1985) Characterization of dopamine receptors mediating inhibition of adenylate cyclase activity in rat striatum. Mol Pharmacol 28: 138–145.

Ouimet C C, Miller P E, Hemmings Jr H C, Walaas S I, Greengard P (1984) DARPP-32, a dopamine- and adenosine 3':5'-monophosphate-regulated phosphoprotein enriched in dopamine-innervated brain regions. III. Immunocytochemical localization. J Neurosci 4: 114–124.

Poirier L J, Sourkes T L (1965) Influence of the substantia nigra on the catecholamine content of the striatum. Brain 88: 181–192.

Polli J W, Kincaid R L (1994) Expression of calmodulin-dependent phosphodiesterase isoform (PDE1B1) correlates with brain regions having extensive dopaminergic innervation. J Neurosci 14: 1251–1261.

Schiffman S N, Lledo P-M, Vincent J-D (1994) Dopamine D1 receptor modulates the voltage-gated sodium current in rat striatal neurons through a protein kinase. Am J Physiol 483: 95–107.

Seeman P (1992) Dopamine receptor sequences. Therapeutic levels of neuroleptics occupy D2 receptors, clozapine occupies D4. Neuropsychopharmacology 7: 261–84.

Seeman P, Van Tol H H (1994) Dopamine receptor pharmacology. Trends in Pharmacol Sci 15: 264–70.

Sibley DR, Monsma Jr FJ (1992) Molecular biology of dopamine receptors. Trends in Pharmacol Sci 13: 61–69.

Sipes, T. A., and Geyer, M. A. (1995). 8-OH-DPAT disruption of prepule inhibition in rats: reversal with (+)WAY 100, 135 and localization of site of action. Psychopharmacology 117:41–48.

Snyder G L, Fisone G, Morino P, Gundersen V, Ottersen O P, HÜkfelt T, Greengard P (1993) Regulation by the neuropeptide cholecystokinin (CCK-8S) of protein phosphorylation in the neostriatum. Proc Natl Acad Sci, USA 90: 11277–11281.

Snyder G L, Girault J-A, Chen J YC, Czernik A J, Kebabian J W, Nathanson J A, Greengard P (1992) Phosphorylation of DARPP-32 and protein phosphatase inhibitor-1 in rat choroid plexus: Regulation by factors other than dopamine. J Neurosci 12: 3071–3083.

Snyder G L, Fienberg A, Dulubova I, Nairn A C, Greengard P (1996) Dopamine-mediated phosphorylation of NMDA-R1 in the rat nucleus accumbens. Soc. Neurosci. Abst. 22: 380.

Stoof J C, Kebabian J W (1981) Opposing roles for D-1 and D-2 dopamine receptors in efflux of cyclic AMP from rat neostriatum. Nature 294: 366–8.

Surmeier D J, Bargas J, Hemmings Jr H C, Nairn A C, Greengard P (1994) Differential modulation of calcium currents by the D1 dopaminergic signaling pathway in rat neostriatal neurons. Neuron 14: 385–397.

Surmeier D J. Eberwine J, Wilson C J, Cao Y, Stefani A, Kitai S T (1992) Dopamine receptor subtypes colocalize in rat striatonigral neurons. Proc. Natl. Acad. Sci., USA 89: 10178–10182.

Surmeier D J, Song W J, Yan Z (1996) Coordinated expression of dopamine receptors in neostriatal medium spiny neurons. J Neurosci 16: 6579–91.

Swanson L W (1982) The projections of the ventral tegmental area and adjacent regions: a combined fluorescent retrograde tracer and immunofluorescence study in the rat. Brain Res Bull 9: 321–353.

Swerdlow, N., Braff, D. L., Caine, S. B., and Geyer. M. A. (1993). Limbic corticostriato-pallido-pontine substrates of sensorimotor gating in animal models and psychiatric disorders. In Limbic motor circuits and neuropsychiatry, P. W. Kalivas, Barnes, C. D., ed. (Boca Raton: CRC Press), pp.311–328.

Thastrup O, Cullen P. J., Drobak B K, Hanley M R, Dawson A P (1990) Thapsigargin, a tumor promoter, discharges intracellular $Ca^{2+}$ stores by specific inhibition of the endoplasmic reticulum $Ca^{2+}$-ATPase. Proc Natl Acad Sci, USA 87: 2466–70.

Towbin H, Staehlin T, Gordon J (1979) Electrophoretic transfer of proteins from polyacrylamide gels to nitrocellulose sheets: procedure and some applications. Proc Natl Acad Sci, USA 76: 4350–4354.

Vallar L, Muca C, Magni M, Albert P, Bunzow J, Meldolesi J, Civelli O (1990) Differential coupling of dopaminergic D2 receptors expressed in different cell types. J Biol Chem 265: 10320–6.

Walaas S I, Aswad D W, Greengard P (1983) A dopamine- and cyclic AMP-regulated phosphoprotein enriched in dopamine-innervated brain regions. Nature 301: 69–71.

Walaas SI, Greengard P (1984) DARPP-32, a dopamine- and adenosine 3':5'-monophosphate-regulated phosphoprotein enriched in dopamine-innervated brain regions. I. Regional and cellular distribution in rat brain. J Neurosci 4: 84–98.

Williams K R, Hemmings Jr H C, LoPresti M B, Konigsberg W E, Greengard P (1986) DARPP-32, a dopamine- and cyclic AMP-regulated neuronal phosphoprotein. Primary structure and homology with protein phosphatase inhibitor-1. J Biol Chem 261: 1890–1903.

Yan Z, Song W-J, Surmeier DJ (1996) Activation of D2 dopamine receptors reduces $Ca^{2+}$ currents in rat neostriatal cholinergic interneurons. Soc. Neurosci. Abst. 26:1088.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

What is claimed is:

1. A method of treating a schizophrenic patient comprising administering to the patient an agent that inhibits the dephosphorylation of $thr^{34}$-phosphorylated DARPP-32 wherein the agent inhibits calcineurin by binding to calcineurin; and wherein the agent can readily pass through the blood brain barrier.

2. The method of claim 1 wherein the agent is FK506.

3. A method of identifying an agent for use in the treatment of a schizophrenic patient comprising:

(a) contacting a potential agent with calcineurin and $thr^{34}$-phosphorylated DARPP-32; and (b) detecting the amount of dephosphorylation of $thr^{34}$-phosphorylated DARPP-32; wherein the agent is identified if a decrease in the dephosphorylation of $thr^{34}$-phosphorylated DARPP-32 is detected in the presence of the potential agent.

4. The method of claim 3 further comprising:

(c) administering the potential agent to a mouse along with a dopamine D2 receptor agonist; wherein the administration of the dopamine D2 receptor agonist alone results in a diminished percentage of prepulse inhibition; and (d) determining the response of the mouse to prepulse inhibition; wherein the agent is identified when the response to prepulse inhibition is statistically significantly increased in the presence of the potential agent relative to that determined in the absence of the potential agent.

5. The method of claim 4 further comprising:

(e) administering the potential agent to a DARPP-32 knockout mouse; wherein the DARPP-32 knockout mouse displays a diminished percent of prepulse inhibition; and (f) determining the response of the knockout mouse to prepulse inhibition; wherein an agent is identified when the response to prepulse inhibition is not statistically significantly increased in the presence of the potential agent relative to that determined in the absence of the potential agent.

* * * * *